(12) United States Patent
Le

(10) Patent No.: US 12,029,472 B2
(45) Date of Patent: Jul. 9, 2024

(54) BIPOLAR ELECTROSURGICAL SEALER AND DIVIDER

(71) Applicant: Applied Medical Resources Corporation, Rancho Santa Margarita, CA (US)

(72) Inventor: Richard Le, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 14 days.

(21) Appl. No.: 18/081,140

(22) Filed: Dec. 14, 2022

(65) Prior Publication Data

US 2023/0210583 A1   Jul. 6, 2023

Related U.S. Application Data

(63) Continuation of application No. 16/578,070, filed on Sep. 20, 2019, now Pat. No. 11,540,871, which is a
(Continued)

(51) Int. Cl.
*A61B 18/14*          (2006.01)
*A61B 17/00*          (2006.01)
(Continued)

(52) U.S. Cl.
CPC ............... *A61B 18/1442* (2013.01); *A61B 2017/00438* (2013.01); *A61B 2017/2939* (2013.01);
(Continued)

(58) Field of Classification Search
CPC ...... A61B 18/1442; A61B 2017/00438; A61B 2017/2939; A61B 2018/00589;
(Continued)

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| DE | 40 24 636 A1 | 2/1992 |
| DE | 40 24 636 C2 | 12/1992 |

(Continued)

OTHER PUBLICATIONS

European Patent Office, Extended European Search Report for European Application No. EP 21215386.0, dated May 24, 2022, 6 pgs.

(Continued)

*Primary Examiner* — Tigist S Demie
(74) *Attorney, Agent, or Firm* — Patrick Ikehara

(57) ABSTRACT

An electrosurgical instrument is provided that captures, compresses, fuses and cuts tissue between upper and lower jaws connected to pivotably movable handles. The instrument includes a force and over compression regulation mechanism that is configured such that in a clamped configuration, the jaws delivers a gripping force between the first jaw and the second jaw between a predetermined minimum force and a predetermined maximum force.

20 Claims, 16 Drawing Sheets

Related U.S. Application Data continuation of application No. 14/973,366, filed on Dec. 17, 2015, now Pat. No. 10,420,603.

(60) Provisional application No. 62/096,255, filed on Dec. 23, 2014.

(51) Int. Cl.
    *A61B 17/29* (2006.01)
    *A61B 18/00* (2006.01)
    *A61B 18/12* (2006.01)

(52) U.S. Cl.
    CPC .............. *A61B 2018/00589* (2013.01); *A61B 2018/00601* (2013.01); *A61B 2018/00607* (2013.01); *A61B 2018/00619* (2013.01); *A61B 2018/0063* (2013.01); *A61B 2018/00922* (2013.01); *A61B 2018/128* (2013.01); *A61B 2018/1455* (2013.01)

(58) Field of Classification Search
    CPC ........... A61B 2018/00607; A61B 2018/00619; A61B 2018/0063; A61B 2018/00922; A61B 2018/128; A61B 2018/1455
    See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 1,935,289 A | 4/1933 | Evans |
| 2,002,594 A | 5/1935 | Wappler et al. |
| 2,031,682 A | 2/1936 | Wappler et al. |
| 2,113,246 A | 4/1938 | Wappler |
| 2,176,479 A | 10/1939 | Willis |
| 2,305,156 A | 4/1941 | Grubel |
| 2,632,661 A | 3/1953 | Cristofv |
| 2,827,056 A | 3/1958 | Degelman |
| 3,085,566 A | 4/1963 | Tolles |
| 3,459,187 A | 8/1969 | Pallotta |
| 3,494,363 A | 2/1970 | Jackson |
| 3,588,710 A | 6/1971 | Masters |
| 3,651,811 A | 3/1972 | Hildebrandt et al. |
| 3,685,518 A | 8/1972 | Beuerle et al. |
| 3,780,416 A | 12/1973 | Rider |
| 3,826,263 A | 7/1974 | Cage |
| 3,911,766 A | 10/1975 | Fridolph |
| 3,920,021 A | 11/1975 | Hiltebrandt |
| 3,938,527 A | 2/1976 | Rioux |
| 3,963,030 A | 6/1976 | Newton |
| 3,970,088 A | 7/1976 | Morrison |
| 3,980,085 A | 9/1976 | Ikuno |
| 3,987,795 A | 10/1976 | Morrison |
| 4,030,501 A | 6/1977 | Archibald |
| 4,041,952 A | 8/1977 | Morrison, Jr. et al. |
| 4,043,342 A | 8/1977 | Morrison |
| 4,060,088 A | 11/1977 | Morrison, Jr. et al. |
| 4,074,718 A | 2/1978 | Morrison, Jr. |
| 4,089,336 A | 6/1978 | Cage |
| 4,092,986 A | 6/1978 | Schneiderman |
| 4,094,320 A | 6/1978 | Newton et al. |
| 4,114,623 A | 9/1978 | Meinke |
| 4,126,137 A | 11/1978 | Archibald |
| 4,154,240 A | 5/1979 | Ikuno |
| 4,171,700 A | 10/1979 | Farin |
| 4,181,131 A | 1/1980 | Ogui |
| 4,188,927 A | 2/1980 | Harris |
| 4,196,734 A | 4/1980 | Harris |
| 4,198,957 A | 4/1980 | Cage et al. |
| 4,198,960 A | 4/1980 | Utsugi |
| 4,200,104 A | 4/1980 | Harris |
| 4,231,372 A | 11/1980 | Newton |
| 4,237,887 A | 12/1980 | Gonser |
| 4,244,371 A | 1/1981 | Farin |
| 4,325,374 A | 4/1982 | Komiya |
| 4,331,149 A | 5/1982 | Gonser |
| 4,338,940 A | 7/1982 | Ikuno |
| 4,352,156 A | 9/1982 | Gyugyi |
| 4,370,980 A | 2/1983 | Lottick |
| 4,416,276 A | 11/1983 | Newton |
| 4,416,277 A | 11/1983 | Newton et al. |
| 4,427,014 A | 1/1984 | Bel |
| 4,429,694 A | 2/1984 | McGreevy |
| 4,463,759 A | 8/1984 | Garito et al. |
| 4,487,489 A | 12/1984 | Takamatsu |
| 4,514,619 A | 4/1985 | Kugelman |
| 4,522,206 A | 6/1985 | Whipple et al. |
| 4,552,143 A | 11/1985 | Lottick |
| 4,569,131 A | 2/1986 | Faulk et al. |
| 4,569,345 A | 2/1986 | Manes et al. |
| 4,590,934 A | 5/1986 | Malis et al. |
| 4,599,553 A | 7/1986 | Brennen et al. |
| 4,630,218 A | 12/1986 | Hurley |
| 4,632,109 A | 12/1986 | Paterson |
| 4,644,950 A | 2/1987 | Valli |
| 4,651,280 A | 3/1987 | Chang et al. |
| 4,655,216 A | 4/1987 | Tischer |
| 4,657,018 A | 4/1987 | Hakky |
| 4,658,815 A | 4/1987 | Farin et al. |
| 4,658,819 A | 4/1987 | Harris et al. |
| 4,658,820 A | 4/1987 | Klicek |
| 4,674,498 A | 6/1987 | Stasz |
| 4,685,459 A | 8/1987 | Koch et al. |
| 4,699,146 A | 10/1987 | Sieverding |
| 4,712,545 A | 12/1987 | Honkanen |
| 4,716,897 A | 1/1988 | Noguchi et al. |
| 4,727,874 A | 3/1988 | Bowers |
| 4,739,759 A | 4/1988 | Rexroth et al. |
| 4,741,334 A | 5/1988 | Irnich |
| 4,752,864 A | 6/1988 | Clappier |
| 4,754,757 A | 7/1988 | Feucht |
| 4,788,977 A | 12/1988 | Farin et al. |
| 4,802,476 A | 2/1989 | Noerenberg et al. |
| 4,818,954 A | 4/1989 | Flachenecker |
| 4,827,927 A | 5/1989 | Newton |
| 4,848,335 A | 7/1989 | Manes |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,872,456 A | 10/1989 | Hasson |
| 4,887,612 A | 12/1989 | Esser et al. |
| 4,889,722 A | 12/1989 | Sheffield et al. |
| 4,903,696 A | 2/1990 | Stasz et al. |
| 4,905,691 A | 3/1990 | Rydell |
| 4,922,903 A | 5/1990 | Welch et al. |
| 4,936,281 A | 6/1990 | Stasz |
| 4,937,254 A | 6/1990 | Sheffield et al. |
| 4,938,761 A | 7/1990 | Ensslin |
| 4,942,313 A | 7/1990 | Kinzel |
| 4,958,539 A | 9/1990 | Stasz et al. |
| 4,969,885 A | 11/1990 | Farin |
| 4,976,711 A | 12/1990 | Parins et al. |
| 5,007,908 A | 4/1991 | Rydell |
| 5,013,312 A | 5/1991 | Parins et al. |
| 5,015,227 A | 5/1991 | Broadwin et al. |
| 5,016,521 A | 5/1991 | Haka |
| 5,026,370 A | 6/1991 | Lottick |
| 5,026,371 A | 6/1991 | Rydell et al. |
| 5,035,696 A | 7/1991 | Rydell |
| 5,038,109 A | 8/1991 | Goble et al. |
| 5,047,026 A | 9/1991 | Rydell |
| 5,047,027 A | 9/1991 | Rydell |
| 5,052,402 A | 10/1991 | Bencini et al. |
| 5,057,107 A | 10/1991 | Parins et al. |
| 5,061,269 A | 10/1991 | Muller |
| 5,062,031 A | 10/1991 | Flachenecker et al. |
| 5,071,419 A | 12/1991 | Rydell et al. |
| 5,078,717 A | 1/1992 | Parins et al. |
| 5,083,565 A | 1/1992 | Parins |
| 5,085,659 A | 2/1992 | Rydell |
| 5,087,257 A | 2/1992 | Farin et al. |
| 5,098,431 A | 3/1992 | Rydell |

(56) References Cited

U.S. PATENT DOCUMENTS

| | | |
|---|---|---|
| 5,116,332 A | 5/1992 | Lottick |
| 5,122,137 A | 6/1992 | Lennox |
| 5,125,928 A | 6/1992 | Parins et al. |
| 5,127,412 A | 7/1992 | Cosmetto et al. |
| 5,151,102 A | 9/1992 | Kamiyama et al. |
| 5,158,561 A | 10/1992 | Rydell et al. |
| 5,160,343 A | 11/1992 | Brancel et al. |
| 5,167,658 A | 12/1992 | Ensslin |
| 5,171,255 A | 12/1992 | Rydell |
| 5,171,311 A | 12/1992 | Rydell |
| 5,190,517 A | 3/1993 | Klicek et al. |
| 5,190,541 A | 3/1993 | Abele et al. |
| 5,192,280 A | 3/1993 | Parins |
| 5,197,963 A | 3/1993 | Parins |
| 5,197,964 A | 3/1993 | Parins |
| 5,201,732 A | 4/1993 | Parins et al. |
| 5,217,457 A | 6/1993 | Delahuerga et al. |
| 5,217,458 A | 6/1993 | Parins |
| 5,234,427 A | 8/1993 | Ohtomo et al. |
| 5,244,462 A | 9/1993 | Delahuerga et al. |
| 5,246,440 A | 9/1993 | Van Noord |
| 5,250,047 A | 10/1993 | Rydell |
| 5,250,056 A | 10/1993 | Hasson |
| 5,254,126 A | 10/1993 | Filipi et al. |
| 5,256,149 A | 10/1993 | Banik et al. |
| 5,258,006 A | 11/1993 | Rydell et al. |
| 5,267,997 A | 12/1993 | Farin et al. |
| 5,269,780 A | 12/1993 | Roos |
| 5,273,524 A | 12/1993 | Fox et al. |
| 5,281,216 A | 1/1994 | Klicek |
| 5,282,799 A | 2/1994 | Rydell |
| 5,286,255 A | 2/1994 | Weber |
| 5,290,286 A | 3/1994 | Parins |
| 5,300,070 A | 4/1994 | Gentelia et al. |
| 5,304,190 A | 4/1994 | Reckelhoff et al. |
| 5,312,329 A | 5/1994 | Beaty et al. |
| 5,314,424 A | 5/1994 | Nicholas |
| 5,318,563 A | 6/1994 | Malis et al. |
| 5,322,055 A | 6/1994 | Davison et al. |
| 5,324,289 A | 6/1994 | Eggers |
| 5,330,471 A | 7/1994 | Eggers |
| 5,334,183 A | 8/1994 | Wuchinich |
| 5,338,317 A | 8/1994 | Hasson et al. |
| 5,341,807 A | 8/1994 | Nardella |
| 5,341,815 A | 8/1994 | Cofone et al. |
| 5,342,359 A | 8/1994 | Rydell |
| 5,342,381 A | 8/1994 | Tidemand |
| 5,352,222 A | 10/1994 | Rydell |
| 5,352,223 A | 10/1994 | McBrayer et al. |
| 5,354,313 A | 10/1994 | Boebel |
| 5,356,408 A | 10/1994 | Rydell |
| 5,370,645 A | 12/1994 | Klicek et al. |
| 5,372,124 A | 12/1994 | Takayama et al. |
| 5,372,596 A | 12/1994 | Klicek et al. |
| 5,374,277 A | 12/1994 | Hassler |
| 5,382,247 A | 1/1995 | Cimino et al. |
| 5,383,880 A | 1/1995 | Hovven |
| 5,383,922 A | 1/1995 | Zipes et al. |
| 5,387,196 A | 2/1995 | Green et al. |
| 5,387,197 A | 2/1995 | Smith et al. |
| 5,389,104 A | 2/1995 | Hahnen et al. |
| 5,389,849 A | 2/1995 | Asano et al. |
| 5,391,166 A | 2/1995 | Eggers |
| 5,392,917 A | 2/1995 | Alpern et al. |
| 5,400,267 A | 3/1995 | Denen |
| 5,403,312 A | 4/1995 | Yates et al. |
| 5,403,342 A | 4/1995 | Tovey et al. |
| 5,405,344 A | 4/1995 | Williamson et al. |
| 5,409,498 A | 4/1995 | Braddock et al. |
| 5,417,687 A | 5/1995 | Nardella et al. |
| 5,422,567 A | 6/1995 | Matsunaga |
| 5,423,808 A | 6/1995 | Edwards et al. |
| 5,423,810 A | 6/1995 | Goble et al. |
| 5,431,638 A | 7/1995 | Hennig et al. |
| 5,431,649 A | 7/1995 | Mulier et al. |
| 5,431,674 A | 7/1995 | Basile et al. |
| 5,432,459 A | 7/1995 | Thompson et al. |
| 5,436,566 A | 7/1995 | Thompson et al. |
| 5,437,664 A | 8/1995 | Cohen et al. |
| 5,438,302 A | 8/1995 | Goble |
| 5,443,463 A | 8/1995 | Stern et al. |
| 5,445,142 A | 8/1995 | Hassler, Jr. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,460,182 A | 10/1995 | Goodman et al. |
| 5,462,546 A | 10/1995 | Rydell |
| 5,464,144 A | 11/1995 | Guy et al. |
| 5,472,439 A | 12/1995 | Hurd |
| 5,472,442 A | 12/1995 | Klicek |
| 5,472,443 A | 12/1995 | Cordis et al. |
| 5,472,451 A | 12/1995 | Freitas et al. |
| 5,474,057 A | 12/1995 | Makower et al. |
| 5,476,479 A | 12/1995 | Green et al. |
| 5,478,351 A | 12/1995 | Meade et al. |
| 5,484,400 A | 1/1996 | Edwards et al. |
| 5,486,185 A | 1/1996 | Freitas et al. |
| 5,496,312 A | 3/1996 | Klicek |
| 5,496,317 A | 3/1996 | Goble et al. |
| 5,499,992 A | 3/1996 | Meade et al. |
| 5,499,998 A | 3/1996 | Meade et al. |
| 5,503,320 A | 4/1996 | Webster et al. |
| 5,507,773 A | 4/1996 | Hutema et al. |
| 5,509,916 A | 4/1996 | Taylor et al. |
| 5,514,129 A | 5/1996 | Smith |
| 5,514,134 A | 5/1996 | Rydell et al. |
| 5,518,163 A | 5/1996 | Hooven |
| 5,518,164 A | 5/1996 | Hooven |
| 5,527,313 A | 6/1996 | Scott et al. |
| 5,527,330 A | 6/1996 | Tovey |
| 5,531,744 A | 7/1996 | Nardella et al. |
| 5,540,681 A | 7/1996 | Strul et al. |
| 5,540,684 A | 7/1996 | Hassler et al. |
| 5,540,685 A | 7/1996 | Parins et al. |
| 5,541,376 A | 7/1996 | Ladtkow et al. |
| 5,551,945 A | 9/1996 | Yabe et al. |
| 5,558,429 A | 9/1996 | Cain |
| 5,558,671 A | 9/1996 | Yates |
| 5,562,699 A | 10/1996 | Heimberger et al. |
| 5,562,700 A | 10/1996 | Huiterna et al. |
| 5,571,100 A | 11/1996 | Goble et al. |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,573,535 A | 11/1996 | Viklund |
| 5,575,789 A | 11/1996 | Bell et al. |
| 5,575,805 A | 11/1996 | Li |
| 5,584,830 A | 12/1996 | Ladd et al. |
| 5,599,344 A | 2/1997 | Paterson |
| 5,599,350 A | 2/1997 | Schulze et al. |
| 5,603,711 A | 2/1997 | Parins et al. |
| D378,611 S | 3/1997 | Croley |
| 5,607,391 A | 3/1997 | Klinger et al. |
| 5,609,151 A | 3/1997 | Mulier et al. |
| 5,609,560 A | 3/1997 | Ichikawa et al. |
| 5,609,573 A | 3/1997 | Sandock |
| 5,611,709 A | 3/1997 | McAnulty |
| 5,613,966 A | 3/1997 | Makower et al. |
| 5,620,415 A | 4/1997 | Lucey et al. |
| 5,620,447 A | 4/1997 | Smith et al. |
| 5,624,452 A | 4/1997 | Yates |
| 5,626,575 A | 5/1997 | Crenner |
| 5,626,607 A | 5/1997 | Malecki et al. |
| 5,626,608 A | 5/1997 | Cuny et al. |
| 5,627,584 A | 5/1997 | Nishikori et al. |
| 5,633,578 A | 5/1997 | Eggers et al. |
| 5,645,540 A | 7/1997 | Henniges et al. |
| 5,647,869 A | 7/1997 | Goble et al. |
| 5,651,780 A | 7/1997 | Jackson et al. |
| 5,658,279 A | 8/1997 | Nardella et al. |
| 5,658,281 A | 8/1997 | Heard |

(56) References Cited

U.S. PATENT DOCUMENTS

| | | |
|---|---|---|
| 5,665,100 A | 9/1997 | Yoon |
| 5,665,105 A | 9/1997 | Furnish et al. |
| 5,667,517 A | 9/1997 | Hooven |
| 5,669,907 A | 9/1997 | Platt, Jr. et al. |
| 5,674,184 A | 10/1997 | Hassler, Jr. |
| 5,674,220 A | 10/1997 | Fox et al. |
| 5,683,349 A | 11/1997 | Makower et al. |
| 5,688,270 A | 11/1997 | Yates et al. |
| 5,693,045 A | 12/1997 | Eggers |
| 5,693,051 A | 12/1997 | Schulze et al. |
| 5,695,494 A | 12/1997 | Becker |
| 5,697,281 A | 12/1997 | Eggers et al. |
| 5,697,909 A | 12/1997 | Eggers et al. |
| 5,700,261 A | 12/1997 | Brinkerhoff |
| 5,702,386 A | 12/1997 | Stern et al. |
| 5,702,387 A | 12/1997 | Arts et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,128 A | 2/1998 | Schrenk et al. |
| 5,713,895 A | 2/1998 | Lontine et al. |
| 5,713,896 A | 2/1998 | Nardella |
| 5,720,293 A | 2/1998 | Quinn et al. |
| 5,720,742 A | 2/1998 | Zacharias |
| 5,720,744 A | 2/1998 | Eggleston et al. |
| 5,720,745 A | 2/1998 | Farin et al. |
| 5,722,975 A | 3/1998 | Edwards et al. |
| 5,725,524 A | 3/1998 | Mulier et al. |
| 5,735,848 A | 4/1998 | Yates et al. |
| 5,735,849 A | 4/1998 | Baden et al. |
| 5,743,456 A | 4/1998 | Jones et al. |
| 5,743,906 A | 4/1998 | Parins et al. |
| 5,746,210 A | 5/1998 | Benaron et al. |
| 5,746,740 A | 5/1998 | Nicholas |
| 5,746,759 A | 5/1998 | Meade et al. |
| 5,752,519 A | 5/1998 | Benaron et al. |
| 5,755,717 A | 5/1998 | Yates et al. |
| 5,759,185 A | 6/1998 | Grinberg |
| 5,762,609 A | 6/1998 | Benaron et al. |
| 5,766,167 A | 6/1998 | Eggers et al. |
| 5,769,791 A | 6/1998 | Benaron et al. |
| 5,769,841 A | 6/1998 | Odell et al. |
| 5,772,597 A | 6/1998 | Goldberger et al. |
| 5,772,659 A | 6/1998 | Becker et al. |
| 5,772,660 A | 6/1998 | Young et al. |
| 5,776,092 A | 7/1998 | Farin et al. |
| 5,776,129 A | 7/1998 | Mersch |
| 5,776,130 A | 7/1998 | Buysse et al. |
| 5,776,155 A | 7/1998 | Beaupre et al. |
| 5,782,397 A | 7/1998 | Koukline |
| 5,785,658 A | 7/1998 | Benaron et al. |
| 5,792,139 A | 8/1998 | Chambers et al. |
| 5,792,178 A | 8/1998 | Welch et al. |
| 5,797,906 A | 8/1998 | Rhum et al. |
| 5,797,938 A | 8/1998 | Paraschac et al. |
| 5,797,941 A | 8/1998 | Schulze |
| 5,800,449 A | 9/1998 | Wales |
| 5,807,261 A | 9/1998 | Benaron et al. |
| 5,807,393 A | 9/1998 | Williamson, IV et al. |
| 5,807,395 A | 9/1998 | Mulier et al. |
| 5,810,806 A | 9/1998 | Ritchart et al. |
| 5,810,811 A | 9/1998 | Yates et al. |
| 5,810,859 A | 9/1998 | Dimatteo et al. |
| 5,817,091 A | 10/1998 | Nardella et al. |
| 5,817,093 A | 10/1998 | Williamson, IV et al. |
| 5,817,119 A | 10/1998 | Klieman et al. |
| 5,827,271 A | 10/1998 | Buysse et al. |
| 5,827,279 A | 10/1998 | Hughett et al. |
| 5,827,299 A | 10/1998 | Thomason et al. |
| 5,830,231 A | 11/1998 | Geiges, Jr. |
| 5,833,690 A | 11/1998 | Yates et al. |
| 5,836,942 A | 11/1998 | Netherly et al. |
| 5,836,943 A | 11/1998 | Miller, III |
| 5,846,194 A | 12/1998 | Wasson et al. |
| 5,849,020 A | 12/1998 | Long et al. |
| 5,853,412 A | 12/1998 | Mayenbergr |
| 5,860,975 A | 1/1999 | Goble et al. |
| 5,873,873 A | 2/1999 | Smith et al. |
| 5,876,398 A | 3/1999 | Mulier et al. |
| 5,876,401 A | 3/1999 | Schulze et al. |
| 5,885,277 A | 3/1999 | Korth |
| 5,891,095 A | 4/1999 | Eggers et al. |
| 5,891,141 A | 4/1999 | Rydell |
| 5,891,142 A | 4/1999 | Eggers et al. |
| 5,893,835 A | 4/1999 | Witt et al. |
| 5,893,873 A | 4/1999 | Rader et al. |
| 5,897,490 A | 4/1999 | Fox et al. |
| 5,897,523 A | 4/1999 | Wright et al. |
| 5,897,553 A | 4/1999 | Mulier et al. |
| 5,897,569 A | 4/1999 | Kellogg et al. |
| 5,902,264 A | 5/1999 | Toso et al. |
| 5,902,301 A | 5/1999 | Olig |
| 5,904,709 A | 5/1999 | Dicky et al. |
| 5,906,613 A | 5/1999 | Mulier et al. |
| 5,908,402 A | 6/1999 | Blythe |
| 5,908,420 A | 6/1999 | Parins et al. |
| 5,910,152 A | 6/1999 | Bays |
| 5,928,137 A | 7/1999 | Green |
| 5,928,255 A | 7/1999 | Meade et al. |
| 5,928,256 A | 7/1999 | Riza |
| 5,931,836 A | 8/1999 | Hatta et al. |
| 5,935,126 A | 8/1999 | Riza |
| 5,938,633 A | 8/1999 | Beaupre |
| 5,944,715 A | 8/1999 | Goble et al. |
| 5,944,718 A | 8/1999 | Austin et al. |
| 5,944,737 A | 8/1999 | Tsonton et al. |
| 5,947,284 A | 9/1999 | Foster |
| 5,947,984 A | 9/1999 | Whipple |
| 5,951,552 A | 9/1999 | Long et al. |
| 5,954,736 A | 9/1999 | Bishop et al. |
| 5,954,746 A | 9/1999 | Holthaus et al. |
| 5,957,943 A | 9/1999 | Vaitekunas |
| 5,961,514 A | 10/1999 | Long et al. |
| 5,968,062 A | 10/1999 | Thomas et al. |
| 5,968,074 A | 10/1999 | Prestel |
| 5,976,077 A | 11/1999 | Wittens et al. |
| 5,976,128 A | 11/1999 | Schilling et al. |
| 5,980,510 A | 11/1999 | Tsonton et al. |
| 5,980,516 A | 11/1999 | Mulier et al. |
| 5,984,921 A | 11/1999 | Long et al. |
| 5,987,346 A | 11/1999 | Benaron et al. |
| 5,993,380 A | 11/1999 | Yabe et al. |
| 5,993,447 A | 11/1999 | Blewett et al. |
| 5,995,875 A | 11/1999 | Blewett et al. |
| 5,997,533 A | 12/1999 | Kuhns |
| 6,003,517 A | 12/1999 | Sheffield et al. |
| 6,004,319 A | 12/1999 | Goble et al. |
| 6,004,335 A | 12/1999 | Vaitekunas et al. |
| 6,010,499 A | 1/2000 | Cobb |
| 6,010,516 A | 1/2000 | Hulka |
| 6,013,076 A | 1/2000 | Goble et al. |
| 6,015,406 A | 1/2000 | Goble et al. |
| 6,016,809 A | 1/2000 | Mulier et al. |
| D420,741 S | 2/2000 | Croley |
| 6,024,741 A | 2/2000 | Williamson, IV et al. |
| 6,024,744 A | 2/2000 | Kese et al. |
| 6,027,501 A | 2/2000 | Goble et al. |
| 6,027,522 A | 2/2000 | Palmer |
| 6,030,384 A | 2/2000 | Nezhat |
| 6,030,402 A | 2/2000 | Thompson et al. |
| 6,033,399 A | 3/2000 | Gines |
| 6,033,404 A | 3/2000 | Melzer et al. |
| 6,036,657 A | 3/2000 | Milliman et al. |
| 6,039,733 A | 3/2000 | Buysse et al. |
| 6,039,734 A | 3/2000 | Goble et al. |
| 6,039,736 A | 3/2000 | Platt, Jr. |
| 6,050,996 A | 4/2000 | Schmaltz et al. |
| 6,051,010 A | 4/2000 | Dimatteo et al. |
| 6,053,172 A | 4/2000 | Hovda et al. |
| 6,053,914 A | 4/2000 | Eggers et al. |
| 6,056,746 A | 5/2000 | Goble et al. |
| 6,063,050 A | 5/2000 | Manna et al. |
| 6,063,075 A | 5/2000 | Mohori |
| 6,063,081 A | 5/2000 | Mulier et al. |

(56) References Cited

U.S. PATENT DOCUMENTS

| | | |
|---|---|---|
| 6,063,086 A | 5/2000 | Benecke et al. |
| 6,066,139 A | 5/2000 | Ryan et al. |
| 6,068,627 A | 5/2000 | Orszulak et al. |
| 6,068,647 A | 5/2000 | Witt et al. |
| 6,070,444 A | 6/2000 | Lontine et al. |
| 6,074,386 A | 6/2000 | Goble et al. |
| RE36,795 E | 7/2000 | Rydell |
| 6,083,191 A | 7/2000 | Rose |
| 6,086,586 A | 7/2000 | Hooven |
| 6,090,106 A | 7/2000 | Goble et al. |
| 6,090,120 A | 7/2000 | Wright et al. |
| 6,092,722 A | 7/2000 | Heinrichs et al. |
| 6,093,186 A | 7/2000 | Goble |
| 6,096,037 A | 8/2000 | Mulier et al. |
| 6,102,909 A | 8/2000 | Chen et al. |
| 6,106,521 A | 8/2000 | Blewett et al. |
| 6,109,268 A | 8/2000 | Thapliyal et al. |
| 6,110,171 A | 8/2000 | Rydell |
| 6,113,591 A | 9/2000 | Whayne et al. |
| 6,113,594 A | 9/2000 | Savage |
| 6,113,596 A | 9/2000 | Hooven et al. |
| 6,113,598 A | 9/2000 | Baker |
| 6,117,152 A | 9/2000 | Huitema |
| 6,120,501 A | 9/2000 | Long et al. |
| H1904 H | 10/2000 | Yates |
| 6,132,429 A | 10/2000 | Baker |
| 6,135,998 A | 10/2000 | Palanker |
| 6,139,519 A | 10/2000 | Blythe |
| 6,139,547 A | 10/2000 | Lontine et al. |
| 6,142,992 A | 11/2000 | Cheng et al. |
| 6,152,923 A | 11/2000 | Ryan |
| 6,159,146 A | 12/2000 | El Gazayerli |
| 6,162,235 A | 12/2000 | Vaitekunas |
| 6,165,175 A | 12/2000 | Wampler et al. |
| 6,168,605 B1 | 1/2001 | Measamer et al. |
| 6,171,304 B1 | 1/2001 | Netherly et al. |
| 6,174,308 B1 | 1/2001 | Goble et al. |
| 6,174,309 B1 | 1/2001 | Wrublewski et al. |
| 6,179,834 B1 | 1/2001 | Buysse et al. |
| 6,186,147 B1 | 2/2001 | Cobb |
| 6,187,003 B1 | 2/2001 | Buysse et al. |
| 6,187,026 B1 | 2/2001 | Devlin et al. |
| 6,190,383 B1 | 2/2001 | Schmaltz et al. |
| 6,190,385 B1 | 2/2001 | Tom et al. |
| 6,190,386 B1 | 2/2001 | Rydell |
| 6,193,129 B1 | 2/2001 | Bittner et al. |
| 6,193,653 B1 | 2/2001 | Evans et al. |
| 6,193,713 B1 | 2/2001 | Geistert et al. |
| 6,197,026 B1 | 3/2001 | Farin et al. |
| 6,203,541 B1 | 3/2001 | Keppel |
| 6,206,823 B1 | 3/2001 | Kolata et al. |
| 6,206,844 B1 | 3/2001 | Reichel et al. |
| 6,206,875 B1 | 3/2001 | Long et al. |
| 6,206,877 B1 | 3/2001 | Kese et al. |
| 6,210,403 B1 | 4/2001 | Klicek |
| 6,210,405 B1 | 4/2001 | Goble et al. |
| 6,214,003 B1 | 4/2001 | Morgan et al. |
| 6,214,023 B1 | 4/2001 | Whipple et al. |
| 6,228,023 B1 | 5/2001 | Zaslavsky et al. |
| 6,228,055 B1 | 5/2001 | Foerster et al. |
| 6,228,080 B1 | 5/2001 | Gines |
| 6,228,081 B1 | 5/2001 | Goble |
| 6,228,083 B1 | 5/2001 | Lands et al. |
| 6,234,178 B1 | 5/2001 | Goble et al. |
| 6,237,604 B1 | 5/2001 | Burnside et al. |
| 6,238,366 B1 | 5/2001 | Savage et al. |
| 6,238,392 B1 | 5/2001 | Long |
| 6,238,393 B1 | 5/2001 | Mulier et al. |
| 6,242,741 B1 | 6/2001 | Miller et al. |
| 6,246,912 B1 | 6/2001 | Sluijter et al. |
| 6,251,106 B1 | 6/2001 | Becker et al. |
| 6,251,110 B1 | 6/2001 | Wampler |
| 6,254,623 B1 | 7/2001 | Haibel et al. |
| 6,257,241 B1 | 7/2001 | Wampler |
| 6,258,085 B1 | 7/2001 | Eggleston |
| 6,261,286 B1 | 7/2001 | Goble et al. |
| 6,267,761 B1 | 7/2001 | Ryan |
| 6,270,497 B1 | 8/2001 | Sekino et al. |
| 6,273,862 B1 | 8/2001 | Privitera et al. |
| 6,277,114 B1 | 8/2001 | Bullivant et al. |
| 6,277,115 B1 | 8/2001 | Saadat |
| 6,277,117 B1 | 8/2001 | Tetzlaff et al. |
| 6,280,398 B1 | 8/2001 | Ritchart et al. |
| 6,280,407 B1 | 8/2001 | Manna et al. |
| 6,280,441 B1 | 8/2001 | Ryan |
| 6,283,963 B1 | 9/2001 | Regula |
| 6,287,344 B1 | 9/2001 | Wampler |
| 6,293,942 B1 | 9/2001 | Goble et al. |
| 6,293,945 B1 | 9/2001 | Parins et al. |
| 6,296,637 B1 | 10/2001 | Thorne et al. |
| 6,296,640 B1 | 10/2001 | Wampler et al. |
| 6,298,550 B1 | 10/2001 | Kirwan, Jr. |
| 6,302,903 B1 | 10/2001 | Mulier et al. |
| 6,306,131 B1 | 10/2001 | Hareyama et al. |
| 6,306,134 B1 | 10/2001 | Goble et al. |
| 6,308,089 B1 | 10/2001 | von der Ruhr et al. |
| 6,309,400 B2 | 10/2001 | Beaupre |
| 6,312,426 B1 | 11/2001 | Goldberg et al. |
| 6,315,777 B1 | 11/2001 | Comben |
| 6,319,221 B1 | 11/2001 | Savage et al. |
| 6,322,494 B1 | 11/2001 | Bullivant et al. |
| 6,322,549 B1 | 11/2001 | Eggers et al. |
| 6,322,561 B1 | 11/2001 | Eggers et al. |
| 6,325,795 B1 | 12/2001 | Lindemann et al. |
| 6,325,799 B1 | 12/2001 | Goble |
| 6,325,811 B1 | 12/2001 | Messerly |
| 6,328,736 B1 | 12/2001 | Mulier et al. |
| 6,328,751 B1 | 12/2001 | Beaupre |
| 6,331,181 B1 | 12/2001 | Tierney et al. |
| 6,334,068 B1 | 12/2001 | Hacker |
| 6,334,861 B1 | 1/2002 | Chandler et al. |
| 6,336,926 B1 | 1/2002 | Goble et al. |
| 6,348,051 B1 | 2/2002 | Farin et al. |
| 6,352,532 B1 | 3/2002 | Kramer et al. |
| 6,352,536 B1 | 3/2002 | Buysse et al. |
| 6,358,248 B1 | 3/2002 | Mulier et al. |
| 6,358,249 B1 | 3/2002 | Chen et al. |
| 6,358,267 B1 | 3/2002 | Murakami |
| 6,361,534 B1 | 3/2002 | Chen et al. |
| 6,364,877 B1 | 4/2002 | Goble et al. |
| 6,364,879 B1 | 4/2002 | Chen et al. |
| 6,371,967 B1 | 4/2002 | Long et al. |
| D457,958 S | 5/2002 | Dycus |
| 6,383,183 B1 | 5/2002 | Sekino et al. |
| 6,387,092 B1 | 5/2002 | Burnside et al. |
| 6,387,109 B1 | 5/2002 | Davison et al. |
| 6,391,024 B1 | 5/2002 | Sun et al. |
| 6,391,025 B1 | 5/2002 | Weinstein et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,747 B1 | 6/2002 | Lindemann et al. |
| 6,402,748 B1 | 6/2002 | Schoenman et al. |
| 6,406,475 B1 | 6/2002 | Wenzler et al. |
| 6,409,722 B1 | 6/2002 | Hoey et al. |
| 6,409,724 B1 | 6/2002 | Penny et al. |
| 6,409,728 B1 | 6/2002 | Ehr et al. |
| 6,416,486 B1 | 7/2002 | Wampler |
| 6,416,509 B1 | 7/2002 | Goble et al. |
| 6,423,057 B1 | 7/2002 | He et al. |
| 6,423,082 B1 | 7/2002 | Houser et al. |
| 6,432,118 B1 | 8/2002 | Messerly |
| 6,436,096 B1 | 8/2002 | Hareyama |
| 6,440,130 B1 | 8/2002 | Mulier et al. |
| 6,443,952 B1 | 9/2002 | Mulier et al. |
| 6,443,968 B1 | 9/2002 | Holthaus et al. |
| 6,443,970 B1 | 9/2002 | Schulze et al. |
| 6,451,013 B1 | 9/2002 | Bays et al. |
| 6,451,018 B1 | 9/2002 | Lands et al. |
| 6,454,764 B1 | 9/2002 | Fleenor et al. |
| 6,454,781 B1 | 9/2002 | Witt et al. |
| 6,454,782 B1 | 9/2002 | Schwemberger |

(56) References Cited

U.S. PATENT DOCUMENTS

| | | |
|---|---|---|
| 6,458,078 B1 | 10/2002 | Luedtke et al. |
| 6,458,128 B1 | 10/2002 | Schulze |
| 6,458,130 B1 | 10/2002 | Frazier et al. |
| 6,458,142 B1 | 10/2002 | Faller et al. |
| 6,461,352 B2 | 10/2002 | Morgan et al. |
| 6,464,689 B1 | 10/2002 | Qin et al. |
| 6,464,702 B2 | 10/2002 | Schulze et al. |
| 6,464,704 B2 | 10/2002 | Schmaltz et al. |
| 6,468,275 B1 | 10/2002 | Wampler et al. |
| 6,468,286 B2 | 10/2002 | Mastri et al. |
| 6,475,217 B1 | 11/2002 | Platt |
| 6,478,030 B1 | 11/2002 | Shaoeton et al. |
| 6,482,202 B1 | 11/2002 | Goble et al. |
| 6,485,490 B2 | 11/2002 | Wampler et al. |
| 6,488,507 B1 | 12/2002 | Stoloff et al. |
| 6,488,680 B1 | 12/2002 | Francischelli et al. |
| 6,491,690 B1 | 12/2002 | Goble et al. |
| 6,491,708 B2 | 12/2002 | Madan et al. |
| 6,493,589 B1 | 12/2002 | Medhkour et al. |
| 6,494,877 B2 | 12/2002 | Odell et al. |
| 6,494,902 B2 | 12/2002 | Hoey et al. |
| 6,497,705 B2 | 12/2002 | Comben |
| 6,500,176 B1 | 12/2002 | Truckai et al. |
| 6,500,188 B2 | 12/2002 | Harper et al. |
| 6,503,263 B2 | 1/2003 | Adams |
| 6,506,189 B1 | 1/2003 | Rittman et al. |
| 6,506,208 B2 | 1/2003 | Hunt et al. |
| 6,510,854 B2 | 1/2003 | Goble et al. |
| 6,511,476 B2 | 1/2003 | Hareyama |
| 6,511,480 B1 | 1/2003 | Tetzlaff et al. |
| 6,514,252 B2 | 2/2003 | Nezhat et al. |
| 6,517,536 B2 | 2/2003 | Hooven et al. |
| 6,517,538 B1 | 2/2003 | Jacob et al. |
| 6,526,320 B2 | 2/2003 | Mitchell |
| 6,527,771 B1 | 3/2003 | Weadock et al. |
| 6,533,784 B2 | 3/2003 | Truckai et al. |
| 6,534,770 B2 | 3/2003 | Miller et al. |
| 6,537,248 B2 | 3/2003 | Mulier et al. |
| 6,537,272 B2 | 3/2003 | Christopherson et al. |
| 6,540,695 B1 | 4/2003 | Burbank et al. |
| 6,543,456 B2 | 4/2003 | Freeman |
| 6,547,783 B1 | 4/2003 | Vilendrer et al. |
| 6,547,786 B1 | 4/2003 | Goble et al. |
| 6,554,829 B2 | 4/2003 | Schulze et al. |
| 6,558,379 B1 | 5/2003 | Batchelor et al. |
| 6,558,383 B2 | 5/2003 | Cunningham et al. |
| 6,561,983 B2 | 5/2003 | Cronin et al. |
| 6,562,037 B2 | 5/2003 | Paton et al. |
| 6,565,559 B2 | 5/2003 | Eggleston |
| 6,565,560 B1 | 5/2003 | Goble et al. |
| 6,569,105 B1 | 5/2003 | Kortenbach et al. |
| 6,569,109 B2 | 5/2003 | Sakurai et al. |
| 6,572,615 B2 | 6/2003 | Schulze et al. |
| 6,579,289 B2 | 6/2003 | Schnitzler |
| 6,582,424 B2 | 6/2003 | Fleenor et al. |
| 6,582,427 B1 | 6/2003 | Goble et al. |
| 6,584,360 B2 | 6/2003 | Francischelli et al. |
| D477,408 S | 7/2003 | Bromley |
| 6,585,732 B2 | 7/2003 | Mulier et al. |
| 6,585,733 B2 | 7/2003 | Wellman |
| 6,585,735 B1 | 7/2003 | Frazier et al. |
| 6,589,200 B1 | 7/2003 | Schwemberger et al. |
| 6,591,719 B1 | 7/2003 | Poole et al. |
| 6,592,582 B2 | 7/2003 | Hess et al. |
| 6,594,518 B1 | 7/2003 | Benaron et al. |
| 6,602,227 B1 | 8/2003 | Cimino et al. |
| 6,602,249 B1 | 8/2003 | Stoddard et al. |
| 6,602,252 B2 | 8/2003 | Mollenauer |
| 6,605,036 B1 | 8/2003 | Wild |
| 6,607,529 B1 | 8/2003 | Jones et al. |
| 6,610,060 B2 | 8/2003 | Mulier et al. |
| 6,611,793 B1 | 8/2003 | Burnside et al. |
| 6,613,048 B2 | 9/2003 | Mulier et al. |
| 6,616,656 B2 | 9/2003 | Brommersma |
| 6,616,660 B1 | 9/2003 | Platt |
| 6,616,661 B2 | 9/2003 | Wellman et al. |
| 6,620,157 B1 | 9/2003 | Dabney et al. |
| 6,620,161 B2 | 9/2003 | Schulze et al. |
| 6,623,482 B2 | 9/2003 | Pendekanti et al. |
| 6,623,515 B2 | 9/2003 | Mulier et al. |
| 6,626,901 B1 | 9/2003 | Treat et al. |
| 6,629,974 B2 | 10/2003 | Penny et al. |
| 6,638,274 B2 | 10/2003 | Yamamoto |
| 6,648,883 B2 | 11/2003 | Francischelli et al. |
| 6,652,514 B2 | 11/2003 | Ellman et al. |
| 6,652,521 B2 | 11/2003 | Schulze |
| 6,656,110 B1 | 12/2003 | Irion et al. |
| 6,656,175 B2 | 12/2003 | Francischelli et al. |
| 6,656,176 B2 | 12/2003 | Hess et al. |
| 6,656,177 B2 | 12/2003 | Truckal et al. |
| 6,660,017 B2 | 12/2003 | Beaupre |
| 6,662,050 B2 | 12/2003 | Olson |
| 6,662,127 B2 | 12/2003 | Wiener et al. |
| 6,663,622 B1 | 12/2003 | Foley et al. |
| 6,663,627 B2 | 12/2003 | Francischelli et al. |
| 6,663,628 B2 | 12/2003 | Peters |
| 6,666,865 B2 | 12/2003 | Platt |
| 6,676,660 B2 | 1/2004 | Wampler et al. |
| 6,678,621 B2 | 1/2004 | Wiener et al. |
| 6,679,882 B1 | 1/2004 | Kornerup |
| 6,682,527 B2 | 1/2004 | Strul |
| 6,682,528 B2 | 1/2004 | Frazier et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,692,450 B1 | 2/2004 | Coleman |
| 6,692,489 B1 | 2/2004 | Heim et al. |
| 6,695,837 B2 | 2/2004 | Howell |
| 6,695,838 B2 | 2/2004 | Wellman et al. |
| 6,695,840 B2 | 2/2004 | Schulze |
| 6,699,240 B2 | 3/2004 | Francischelli et al. |
| 6,706,038 B2 | 3/2004 | Francischelli et al. |
| 6,706,039 B2 | 3/2004 | Mulier et al. |
| 6,709,432 B2 | 3/2004 | Ferek-Petric |
| 6,723,091 B2 | 4/2004 | Goble et al. |
| 6,726,683 B1 | 4/2004 | Shaw |
| 6,726,686 B2 | 4/2004 | Buysse et al. |
| 6,733,498 B2 | 5/2004 | Paton et al. |
| 6,736,810 B2 | 5/2004 | Hoey et al. |
| 6,740,084 B2 | 5/2004 | Ryan |
| 6,740,085 B2 | 5/2004 | Hareyama et al. |
| 6,740,102 B2 | 5/2004 | Hess et al. |
| 6,743,229 B2 | 6/2004 | Buysse et al. |
| 6,752,804 B2 | 6/2004 | Simpson et al. |
| 6,755,825 B2 | 6/2004 | Schoenman et al. |
| 6,755,827 B2 | 6/2004 | Mulier et al. |
| 6,755,841 B2 | 6/2004 | Fraser et al. |
| 6,758,846 B2 | 7/2004 | Goble et al. |
| 6,764,487 B2 | 7/2004 | Mulier et al. |
| 6,770,071 B2 | 8/2004 | Woloszko et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,780 B2 | 8/2004 | Mulier et al. |
| 6,780,180 B1 | 8/2004 | Goble et al. |
| 6,786,906 B1 | 9/2004 | Cobb |
| 6,790,217 B2 | 9/2004 | Schulze et al. |
| 6,796,828 B2 | 9/2004 | Ehr et al. |
| 6,796,981 B2 | 9/2004 | Wham et al. |
| 6,807,444 B2 | 10/2004 | Tu et al. |
| 6,807,968 B2 | 10/2004 | Francischelli et al. |
| 6,808,518 B2 | 10/2004 | Wellman et al. |
| 6,808,525 B2 | 10/2004 | Latterell et al. |
| 6,814,745 B2 | 11/2004 | Prestel |
| 6,821,273 B2 | 11/2004 | Mollenauer |
| 6,827,715 B2 | 12/2004 | Francischelli et al. |
| 6,827,717 B2 | 12/2004 | Brommersma et al. |
| 6,827,725 B2 | 12/2004 | Batchelor et al. |
| 6,830,569 B2 | 12/2004 | Thompson et al. |
| 6,832,111 B2 | 12/2004 | Tu et al. |
| 6,832,985 B2 | 12/2004 | Irion et al. |

(56) References Cited

U.S. PATENT DOCUMENTS

| | | |
|---|---|---|
| 6,832,998 B2 | 12/2004 | Goble |
| 6,835,082 B2 | 12/2004 | Gonnering |
| 6,835,195 B2 | 12/2004 | Schulze et al. |
| 6,837,887 B2 | 1/2005 | Woloszko et al. |
| 6,843,789 B2 | 1/2005 | Goble |
| 6,849,073 B2 | 2/2005 | Hoy et al. |
| 6,852,112 B2 | 2/2005 | Platt |
| 6,855,142 B2 | 2/2005 | Harano et al. |
| 6,855,145 B2 | 2/2005 | Ciarrocca |
| 6,858,028 B2 | 2/2005 | Mulier et al. |
| 6,860,881 B2 | 3/2005 | Sturm |
| 6,860,894 B1 | 3/2005 | Pittman |
| 6,887,240 B1 | 5/2005 | Lands et al. |
| 6,889,694 B2 | 5/2005 | Hooven |
| 6,893,435 B2 | 5/2005 | Goble |
| 6,893,441 B2 | 5/2005 | Brommersma et al. |
| 6,899,710 B2 | 5/2005 | Hooven |
| 6,905,497 B2 | 6/2005 | Truckai et al. |
| 6,905,498 B2 | 6/2005 | Hooven |
| 6,908,472 B2 | 6/2005 | Wiener et al. |
| 6,911,019 B2 | 6/2005 | Mulier et al. |
| 6,913,579 B2 | 7/2005 | Truckai et al. |
| 6,916,318 B2 | 7/2005 | Francischelli et al. |
| 6,918,880 B2 | 7/2005 | Brookner et al. |
| 6,923,803 B2 | 8/2005 | Goble |
| 6,923,804 B2 | 8/2005 | Eggers et al. |
| 6,923,806 B2 | 8/2005 | Hooven et al. |
| 6,926,716 B2 | 8/2005 | Baker et al. |
| 6,929,641 B2 | 8/2005 | Goble et al. |
| 6,929,644 B2 | 8/2005 | Truckai et al. |
| 6,932,810 B2 | 8/2005 | Ryan |
| 6,932,811 B2 | 8/2005 | Hooven et al. |
| 6,937,033 B2 | 8/2005 | Boronkay et al. |
| 6,939,347 B2 | 9/2005 | Thompson |
| 6,942,660 B2 | 9/2005 | Pantera et al. |
| 6,942,662 B2 | 9/2005 | Goble et al. |
| 6,945,972 B2 | 9/2005 | Frigg et al. |
| 6,945,981 B2 | 9/2005 | Donofrio et al. |
| 6,948,503 B2 | 9/2005 | Refior et al. |
| 6,949,098 B2 | 9/2005 | Mulier et al. |
| 6,958,063 B1 | 10/2005 | Soll et al. |
| 6,960,209 B2 | 11/2005 | Clague et al. |
| 6,960,210 B2 | 11/2005 | Lands et al. |
| 6,962,587 B2 | 11/2005 | Johnson et al. |
| 6,962,589 B2 | 11/2005 | Mulier et al. |
| 6,966,907 B2 | 11/2005 | Goble |
| 6,966,909 B2 | 11/2005 | Marshall et al. |
| 6,971,988 B2 | 12/2005 | Orban et al. |
| 6,974,453 B2 | 12/2005 | Woloszko et al. |
| 6,974,454 B2 | 12/2005 | Hooven |
| 6,976,969 B2 | 12/2005 | Messerly |
| 6,979,332 B2 | 12/2005 | Adams |
| 6,984,231 B2 | 1/2006 | Goble et al. |
| 6,984,233 B2 | 1/2006 | Hooven |
| 6,984,826 B2 | 1/2006 | Miller et al. |
| 6,989,010 B2 | 1/2006 | Francischelli et al. |
| 6,994,705 B2 | 2/2006 | Nobis et al. |
| 6,997,735 B2 | 2/2006 | Ehr et al. |
| 6,997,935 B2 | 2/2006 | Anderson et al. |
| 7,001,380 B2 | 2/2006 | Goble |
| 7,001,415 B2 | 2/2006 | Hooven |
| 7,011,657 B2 | 3/2006 | Truckai et al. |
| 7,025,764 B2 | 4/2006 | Paton et al. |
| 7,029,470 B2 | 4/2006 | Francischelli et al. |
| 7,033,351 B2 | 4/2006 | Howell |
| 7,033,354 B2 | 4/2006 | Keppel |
| 7,033,356 B2 | 4/2006 | Latterell |
| 7,041,096 B2 | 5/2006 | Malis |
| 7,041,102 B2 | 5/2006 | Truckai et al. |
| 7,044,948 B2 | 5/2006 | Keppel |
| 7,044,949 B2 | 5/2006 | Orszulak |
| 7,044,950 B2 | 5/2006 | Yamamoto |
| 7,048,687 B1 | 5/2006 | Reuss et al. |
| 7,049,599 B2 | 5/2006 | Miller et al. |
| 7,052,494 B2 | 5/2006 | Goble et al. |
| 7,060,063 B2 | 6/2006 | Marion et al. |
| 7,063,699 B2 | 6/2006 | Hess |
| 7,066,933 B2 | 6/2006 | Hagg |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,090,673 B2 | 8/2006 | Dycus |
| 7,094,202 B2 | 8/2006 | Nobis et al. |
| 7,094,235 B2 | 8/2006 | Francischelli |
| 7,097,644 B2 | 8/2006 | Long |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,104,834 B2 | 9/2006 | Robinson et al. |
| 7,104,989 B2 | 9/2006 | Skarda |
| 7,108,695 B2 | 9/2006 | Witt et al. |
| 7,111,769 B2 | 9/2006 | Wales et al. |
| 7,112,201 B2 | 9/2006 | Truckai et al. |
| RE39,358 E | 10/2006 | Goble |
| 7,116,157 B2 | 10/2006 | Ross |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson |
| 7,125,409 B2 | 10/2006 | Truckai et al. |
| 7,126,125 B2 | 10/2006 | Miller et al. |
| 7,131,445 B2 | 11/2006 | Amoah |
| 7,131,860 B2 | 11/2006 | Sartor |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse |
| D533,942 S | 12/2006 | Kerr et al. |
| 7,147,635 B2 | 12/2006 | Ciarrocca |
| 7,147,637 B2 | 12/2006 | Goble |
| 7,147,638 B2 | 12/2006 | Chapman et al. |
| 7,150,097 B2 | 12/2006 | Sremcich |
| 7,150,748 B2 | 12/2006 | Ebbutt |
| 7,150,749 B2 | 12/2006 | Dycus et al. |
| 7,153,300 B2 | 12/2006 | Goble |
| 7,156,843 B2 | 1/2007 | Skarda |
| 7,156,845 B2 | 1/2007 | Mulier et al. |
| 7,156,846 B2 | 1/2007 | Dycus et al. |
| 7,159,750 B2 | 1/2007 | Racenet et al. |
| 7,160,293 B2 | 1/2007 | Sturm et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,105 B2 | 1/2007 | Mulier et al. |
| 7,169,115 B2 | 1/2007 | Nobis et al. |
| 7,169,144 B2 | 1/2007 | Hoey |
| 7,169,145 B2 | 1/2007 | Isaacson |
| 7,169,146 B2 | 1/2007 | Truckai et al. |
| 7,172,591 B2 | 2/2007 | Harano et al. |
| 7,179,254 B2 | 2/2007 | Pendkanti |
| 7,179,258 B2 | 2/2007 | Buysse et al. |
| 7,182,604 B2 | 2/2007 | Ehr et al. |
| 7,186,252 B2 | 3/2007 | Nobis et al. |
| 7,186,253 B2 | 3/2007 | Truckai et al. |
| 7,187,790 B2 | 3/2007 | Sabol |
| 7,189,231 B2 | 3/2007 | Clague et al. |
| 7,189,232 B2 | 3/2007 | Scholl et al. |
| 7,189,233 B2 | 3/2007 | Truckai et al. |
| 7,191,015 B2 | 3/2007 | Lamson et al. |
| 7,195,627 B2 | 3/2007 | Amoah |
| 7,195,630 B2 | 3/2007 | Ciarrocca |
| 7,195,631 B2 | 3/2007 | Dumbauld |
| 7,204,835 B2 | 4/2007 | Latterell et al. |
| 7,207,471 B2 | 4/2007 | Heinrich et al. |
| 7,207,990 B2 | 4/2007 | Lands et al. |
| D541,938 S | 5/2007 | Kerr et al. |

(56) References Cited

U.S. PATENT DOCUMENTS

| | | |
|---|---|---|
| 7,211,081 B2 | 5/2007 | Goble |
| 7,211,084 B2 | 5/2007 | Goble |
| 7,214,224 B2 | 5/2007 | Goble |
| 7,216,001 B2 | 5/2007 | Hacker et al. |
| 7,220,260 B2 | 5/2007 | Fleming |
| 7,220,951 B2 | 5/2007 | Truckai et al. |
| 7,223,239 B2 | 5/2007 | Schulze et al. |
| 7,223,265 B2 | 5/2007 | Keppel |
| 7,226,447 B2 | 6/2007 | Uchida |
| 7,229,307 B2 | 6/2007 | Ehr et al. |
| 7,232,439 B2 | 6/2007 | Ciarrocca |
| 7,232,440 B2 | 6/2007 | Dumbald et al. |
| 7,235,048 B2 | 6/2007 | Rein et al. |
| 7,235,072 B2 | 6/2007 | Sartor et al. |
| 7,235,073 B2 | 6/2007 | Levine et al. |
| 7,237,708 B1 | 7/2007 | Guy |
| 7,241,296 B2 | 7/2007 | Buysse et al. |
| 7,247,141 B2 | 7/2007 | Makin et al. |
| 7,247,155 B2 | 7/2007 | Hoey et al. |
| 7,250,048 B2 | 7/2007 | Francischelli et al. |
| 7,250,051 B2 | 7/2007 | Francischelli |
| 7,252,667 B2 | 8/2007 | Moses |
| 7,255,694 B2 | 8/2007 | Keppel |
| 7,255,696 B2 | 8/2007 | Goble et al. |
| 7,255,697 B2 | 8/2007 | Dycus et al. |
| 7,259,340 B2 | 8/2007 | Blaha et al. |
| 7,261,711 B2 | 8/2007 | Mulier et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,273,483 B2 | 9/2007 | Weiner et al. |
| 7,276,068 B2 | 10/2007 | Johnson et al. |
| 7,278,994 B2 | 10/2007 | Goble |
| 7,282,048 B2 | 10/2007 | Goble et al. |
| 7,282,049 B2 | 10/2007 | Oraszulak et al. |
| 7,291,161 B2 | 11/2007 | Hooven |
| 7,297,145 B2 | 11/2007 | Woloszko et al. |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,557 B2 | 12/2007 | Wham |
| 7,309,325 B2 | 12/2007 | Mulier et al. |
| 7,309,849 B2 | 12/2007 | Truckai et al. |
| 7,311,560 B2 | 12/2007 | Ehr et al. |
| 7,311,706 B2 | 12/2007 | Schoenman et al. |
| 7,311,707 B2 | 12/2007 | Hagg et al. |
| 7,311,709 B2 | 12/2007 | Truckai et al. |
| 7,322,975 B2 | 1/2008 | Goble et al. |
| 7,329,256 B2 | 2/2008 | Johnson et al. |
| 7,335,997 B2 | 2/2008 | Weiner |
| 7,344,532 B2 | 3/2008 | Goble et al. |
| 7,347,858 B2 | 3/2008 | Francischelli et al. |
| RE40,279 E | 4/2008 | Sluijter et al. |
| D567,943 S | 4/2008 | Moses et al. |
| 7,353,068 B2 | 4/2008 | Tanake et al. |
| 7,354,435 B2 | 4/2008 | Farin et al. |
| 7,354,440 B2 | 4/2008 | Truckai et al. |
| 7,354,443 B2 | 4/2008 | Moll et al. |
| 7,364,577 B2 | 4/2008 | Wham et al. |
| 7,364,578 B2 | 4/2008 | Francischelli et al. |
| 7,364,579 B2 | 4/2008 | Miller et al. |
| 7,367,972 B2 | 5/2008 | Francischelli et al. |
| 7,367,976 B2 | 5/2008 | Lawes et al. |
| 7,371,246 B2 | 5/2008 | Viola |
| 7,377,902 B2 | 5/2008 | Burbank et al. |
| 7,377,918 B2 | 5/2008 | Amoah |
| 7,377,920 B2 | 5/2008 | Buysse et al. |
| RE40,388 E | 6/2008 | Gines |
| 7,381,209 B2 | 6/2008 | Truckai et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,416,101 B2 | 8/2008 | Shelton |
| 7,416,437 B2 | 8/2008 | Sartor et al. |
| 7,419,487 B2 | 9/2008 | Johnson et al. |
| 7,422,139 B2 | 9/2008 | Shelton et al. |
| 7,422,588 B2 | 9/2008 | Mulier et al. |
| 7,424,965 B2 | 9/2008 | Racenet et al. |
| 7,425,835 B2 | 9/2008 | Eisele |
| 7,426,415 B2 | 9/2008 | Kuhner |
| 7,431,720 B2 | 10/2008 | Pendekanti et al. |
| 7,431,721 B2 | 10/2008 | Paton et al. |
| 7,435,249 B2 | 10/2008 | Buysse et al. |
| 7,435,250 B2 | 10/2008 | Francischelli et al. |
| 7,442,167 B2 | 10/2008 | Dunki-Jacobs |
| 7,442,193 B2 | 10/2008 | Shields |
| 7,442,194 B2 | 10/2008 | Dumbauld |
| 7,445,621 B2 | 11/2008 | Dumbauld et al. |
| 7,458,972 B2 | 12/2008 | Keppel |
| 7,464,846 B2 | 12/2008 | Shelton et al. |
| 7,470,272 B2 | 12/2008 | Mulier et al. |
| 7,473,250 B2 | 1/2009 | Makin et al. |
| 7,473,253 B2 | 1/2009 | Dycus et al. |
| 7,476,233 B1 | 1/2009 | Wiener et al. |
| 7,481,808 B2 | 1/2009 | Koyfman et al. |
| 7,491,199 B2 | 2/2009 | Goble et al. |
| 7,497,858 B2 | 3/2009 | Chapelon et al. |
| 7,811,283 B2 | 10/2010 | Moses et al. |
| 7,841,765 B2 | 11/2010 | Keller |
| 8,561,615 B2 | 10/2013 | Pannell et al. |
| 8,784,417 B2 | 7/2014 | Hanna |
| 8,808,288 B2 | 8/2014 | Reschke |
| 9,161,813 B2 | 10/2015 | Benamou |
| 2001/0037110 A1 | 11/2001 | Schmaltz |
| 2001/0039417 A1 | 11/2001 | Harano et al. |
| 2002/0052599 A1 | 5/2002 | Goble |
| 2002/0115997 A1 | 8/2002 | Truckai |
| 2002/0120262 A1 | 8/2002 | Bek |
| 2002/0120266 A1 | 8/2002 | Truckai |
| 2002/0128650 A1 | 9/2002 | McClurken |
| 2002/0151884 A1 | 10/2002 | Hoey et al. |
| 2002/0161363 A1 | 10/2002 | Fodor et al. |
| 2002/0165541 A1 | 11/2002 | Whitman |
| 2002/0188294 A1 | 12/2002 | Couture et al. |
| 2003/0004510 A1 | 1/2003 | Wham |
| 2003/0014052 A1 | 1/2003 | Buysse |
| 2003/0060818 A1 | 3/2003 | Kannenberg et al. |
| 2003/0065327 A1 | 4/2003 | Wellman |
| 2003/0065358 A1 | 4/2003 | Frecker et al. |
| 2003/0069571 A1 | 4/2003 | Treat |
| 2003/0109871 A1 | 6/2003 | Johnson |
| 2003/0114845 A1 | 6/2003 | Paton et al. |
| 2003/0114848 A1 | 6/2003 | Cobb |
| 2003/0114851 A1 | 6/2003 | Truckai et al. |
| 2003/0125728 A1 | 7/2003 | Nezhat et al. |
| 2003/0125731 A1 | 7/2003 | Smith et al. |
| 2003/0125734 A1 | 7/2003 | Mollenauer |
| 2003/0139741 A1 | 7/2003 | Goble et al. |
| 2003/0181910 A1 | 9/2003 | Dycus |
| 2003/0199863 A1 | 10/2003 | Swanson et al. |
| 2003/0199870 A1 | 10/2003 | Truckai |
| 2003/0229344 A1 | 12/2003 | Dycus et al. |
| 2003/0236549 A1 | 12/2003 | Bonadio et al. |
| 2004/0006340 A1 | 1/2004 | Latterell |
| 2004/0010289 A1 | 1/2004 | Biggs et al. |
| 2004/0068274 A1 | 4/2004 | Hooven |
| 2004/0068304 A1 | 4/2004 | Paton et al. |
| 2004/0073247 A1 | 4/2004 | Loshakove et al. |
| 2004/0082946 A1 | 4/2004 | Malis |
| 2004/0092922 A1 | 5/2004 | Kadziauskas et al. |
| 2004/0122423 A1 | 6/2004 | Dycus |
| 2004/0162557 A1 | 8/2004 | Tetzlaff et al. |
| 2004/0193148 A1 | 9/2004 | Wham |
| 2004/0215127 A1 | 10/2004 | Kadziauskas et al. |
| 2004/0225288 A1 | 11/2004 | Buysse |
| 2004/0250419 A1 | 12/2004 | Sremich |
| 2005/0004563 A1 | 1/2005 | Racz et al. |
| 2005/0004564 A1 | 1/2005 | Wham et al. |
| 2005/0015125 A1 | 1/2005 | Mioduski et al. |
| 2005/0021027 A1 | 1/2005 | Shields et al. |
| 2005/0033282 A1 | 2/2005 | Hooven |
| 2005/0033352 A1 | 2/2005 | Zepf |

(56) References Cited

U.S. PATENT DOCUMENTS

| | | |
|---|---|---|
| 2005/0080319 A1 | 4/2005 | Dinkler, II et al. |
| 2005/0090815 A1 | 4/2005 | Francischelli et al. |
| 2005/0096681 A1 | 5/2005 | Desinger et al. |
| 2005/0101951 A1 | 5/2005 | Wham |
| 2005/0107785 A1 | 5/2005 | Dycus |
| 2005/0113817 A1 | 5/2005 | Isaacson |
| 2005/0113819 A1 | 5/2005 | Wham et al. |
| 2005/0113827 A1 | 5/2005 | Dumbauld et al. |
| 2005/0124915 A1 | 6/2005 | Eggers et al. |
| 2005/0124987 A1 | 6/2005 | Goble |
| 2005/0137592 A1 | 6/2005 | Nguyen et al. |
| 2005/0149017 A1 | 7/2005 | Dycus |
| 2005/0159745 A1 | 7/2005 | Truckai |
| 2005/0165444 A1 | 7/2005 | Hart |
| 2005/0192568 A1 | 9/2005 | Truckai et al. |
| 2005/0203504 A1 | 9/2005 | Wham |
| 2005/0234447 A1 | 10/2005 | Paton et al. |
| 2005/0245918 A1 | 11/2005 | Sliwa, Jr. et al. |
| 2005/0245922 A1 | 11/2005 | Goble |
| 2006/0020265 A1 | 1/2006 | Ryan |
| 2006/0041254 A1 | 2/2006 | Francischelli et al. |
| 2006/0052777 A1 | 3/2006 | Dumbauld |
| 2006/0079788 A1 | 4/2006 | Anderson et al. |
| 2006/0079878 A1 | 4/2006 | Houser |
| 2006/0129146 A1 | 6/2006 | Dycus |
| 2006/0161190 A1 | 7/2006 | Gadberry et al. |
| 2006/0167450 A1 | 7/2006 | Johnson |
| 2006/0173453 A1 | 8/2006 | Gruhl |
| 2006/0217697 A1 | 9/2006 | Lau et al. |
| 2006/0217706 A1 | 9/2006 | Lau et al. |
| 2006/0217707 A1 | 9/2006 | Daniel et al. |
| 2006/0224152 A1 | 10/2006 | Behnke et al. |
| 2006/0224158 A1 | 10/2006 | Odom |
| 2006/0247498 A1 | 11/2006 | Bonadio et al. |
| 2006/0271042 A1 | 11/2006 | Latterell et al. |
| 2007/0016185 A1 | 1/2007 | Tullis et al. |
| 2007/0043352 A1 | 2/2007 | Garrison et al. |
| 2007/0043353 A1 | 2/2007 | Dycus |
| 2007/0062017 A1 | 3/2007 | Dycus et al. |
| 2007/0088202 A1 | 4/2007 | Albrecht et al. |
| 2007/0090788 A1 | 4/2007 | Hansford et al. |
| 2007/0093800 A1 | 4/2007 | Wham et al. |
| 2007/0123847 A1 | 5/2007 | Mihori |
| 2007/0135811 A1 | 6/2007 | Hooven |
| 2007/0142833 A1 | 6/2007 | Dycus |
| 2007/0142834 A1 | 6/2007 | Dumbauld |
| 2007/0156139 A1 | 7/2007 | Schecter |
| 2007/0156140 A1 | 7/2007 | Baily |
| 2007/0167941 A1 | 7/2007 | Hamel et al. |
| 2007/0173811 A1 | 7/2007 | Couture et al. |
| 2007/0173813 A1 | 7/2007 | Odom |
| 2007/0173814 A1 | 7/2007 | Hixson et al. |
| 2007/0179499 A1 | 8/2007 | Garrison |
| 2007/0191827 A1 | 8/2007 | Lishinsky et al. |
| 2007/0191828 A1 | 8/2007 | Houser et al. |
| 2007/0203481 A1 | 8/2007 | Gregg et al. |
| 2007/0213712 A1 | 9/2007 | Buysse et al. |
| 2007/0260242 A1 | 11/2007 | Dycus et al. |
| 2007/0276363 A1 | 11/2007 | Patton et al. |
| 2007/0282195 A1 | 12/2007 | Masini et al. |
| 2007/0282320 A1 | 12/2007 | Buysse et al. |
| 2007/0282332 A1 | 12/2007 | Witt et al. |
| 2007/0287997 A1 | 12/2007 | Tolmei |
| 2008/0009860 A1 | 1/2008 | Odom |
| 2008/0015563 A1 | 1/2008 | Hoey et al. |
| 2008/0015564 A1 | 1/2008 | Wham et al. |
| 2008/0015567 A1 | 1/2008 | Kimura |
| 2008/0030206 A1 | 2/2008 | Podhajsky et al. |
| 2008/0039831 A1 | 2/2008 | Odom et al. |
| 2008/0045947 A1 | 2/2008 | Johnson et al. |
| 2008/0058802 A1 | 3/2008 | Couture |
| 2008/0082098 A1 | 4/2008 | Tanaka et al. |
| 2008/0091189 A1 | 4/2008 | Carlton |
| 2008/0114356 A1 | 5/2008 | Johnson et al. |
| 2008/0125772 A1 | 5/2008 | Stone et al. |
| 2008/0132893 A1 | 6/2008 | D'Amelio et al. |
| 2008/0167651 A1 | 7/2008 | Tetzlaff et al. |
| 2008/0172048 A1 | 7/2008 | Martin |
| 2008/0188848 A1 | 8/2008 | Deutmeyer et al. |
| 2008/0208246 A1 | 8/2008 | Livneh |
| 2008/0215048 A1* | 9/2008 | Hafner ............... A61B 18/1442 606/42 |
| 2008/0215050 A1 | 9/2008 | Bakos |
| 2008/0215051 A1 | 9/2008 | Buysse et al. |
| 2008/0221565 A1 | 9/2008 | Eder et al. |
| 2008/0228179 A1 | 9/2008 | Eder et al. |
| 2008/0294222 A1 | 11/2008 | Schecter |
| 2008/0300589 A1 | 12/2008 | Paul et al. |
| 2008/0300590 A1 | 12/2008 | Horne et al. |
| 2008/0300591 A1 | 12/2008 | Darin et al. |
| 2009/0012520 A1 | 1/2009 | Hixson et al. |
| 2009/0024126 A1 | 1/2009 | Artale |
| 2009/0248007 A1 | 1/2009 | Falkenstein et al. |
| 2009/0275490 A1 | 5/2009 | Malackowski |
| 2009/0171350 A1 | 7/2009 | Dycus et al. |
| 2009/0171352 A1 | 7/2009 | Sutter |
| 2009/0270852 A1 | 10/2009 | Takashino et al. |
| 2011/0257680 A1* | 10/2011 | Reschke ............ A61B 18/1442 606/206 |
| 2012/0010614 A1 | 1/2012 | Couture |
| 2012/0059371 A1 | 3/2012 | Anderson et al. |
| 2012/0083785 A1 | 4/2012 | Roy et al. |
| 2012/0136347 A1 | 5/2012 | Brustad et al. |
| 2012/0197243 A1 | 8/2012 | Sherman et al. |
| 2012/0215220 A1 | 8/2012 | Manzo et al. |
| 2013/0018411 A1 | 1/2013 | Collings et al. |
| 2013/0046295 A1 | 2/2013 | Kerr et al. |
| 2013/0138101 A1 | 5/2013 | Kerr |
| 2013/0138102 A1 | 5/2013 | Twomey et al. |
| 2013/0197874 A1 | 8/2013 | Heckel |
| 2013/0267951 A1 | 10/2013 | Twomey |
| 2013/0274743 A1 | 10/2013 | Banfalvi |
| 2013/0296843 A1* | 11/2013 | Boudreaux ............ A61B 18/18 606/33 |
| 2013/0345696 A1 | 12/2013 | Behnke, II et al. |
| 2014/0005658 A1 | 1/2014 | Rosenbegr |
| 2014/0031821 A1* | 1/2014 | Garrison ............ A61B 17/282 606/171 |
| 2014/0088583 A1 | 3/2014 | Singh |
| 2014/0214019 A1 | 7/2014 | Baxter, III et al. |
| 2016/0310203 A1 | 10/2016 | Gaspredes et al. |
| 2016/0310204 A1 | 10/2016 | McHenry et al. |

FOREIGN PATENT DOCUMENTS

| | | |
|---|---|---|
| DE | 10 2005 044 918 A1 | 2/2007 |
| EP | 0 315 338 A1 | 5/1989 |
| EP | 0 538 984 A2 | 4/1993 |
| EP | 0 570 675 B1 | 11/1993 |
| EP | 0 598 202 B1 | 5/1994 |
| EP | 0 717 967 A2 | 6/1996 |
| EP | 0 737 447 A1 | 10/1996 |
| EP | 0 878 168 A1 | 11/1998 |
| EP | 1 054 637 B1 | 11/2000 |
| EP | 1 157 666 A1 | 11/2001 |
| EP | 1 500 378 A1 | 1/2005 |
| EP | 1 535 581 A2 | 6/2005 |
| EP | 1 545 361 B1 | 6/2005 |
| EP | 1 557 129 A1 | 7/2005 |
| EP | 1 634 539 A1 | 3/2006 |
| EP | 1 728 475 A2 | 12/2006 |
| EP | 1 810 628 A1 | 7/2007 |
| EP | 1 634 539 B1 | 2/2008 |
| EP | 1 665 995 A1 | 2/2008 |
| EP | 1 946 715 A1 | 7/2008 |
| EP | 2 106 762 A1 | 7/2009 |
| EP | 2 158 867 A1 | 8/2009 |
| EP | 2 111 812 A2 | 10/2009 |
| EP | 2 156 802 A2 | 2/2010 |
| EP | 2 301 462 A1 | 3/2011 |
| EP | 2 340 792 A1 | 7/2011 |
| EP | 2 436 327 | 4/2012 |
| EP | 2 436 330 A1 | 4/2012 |

(56) References Cited

FOREIGN PATENT DOCUMENTS

| | | |
|---|---|---|
| EP | 2 574 300 A1 | 4/2013 |
| EP | 2 712 568 A2 | 4/2014 |
| EP | 2 777 578 A1 | 9/2014 |
| EP | 3 369 392 A2 | 9/2018 |
| GB | 2 157 175 A | 10/1985 |
| GB | 2 462 453 A | 8/2008 |
| JP | 60-30946 A | 2/1994 |
| JP | 83-17935 A | 12/1996 |
| JP | 11-070123 A | 3/1999 |
| JP | 11-070124 A | 3/1999 |
| JP | 11-178833 A | 7/1999 |
| JP | 2000-254135 A | 9/2000 |
| JP | 2003-135481 A | 5/2003 |
| JP | 2003-164463 A | 6/2003 |
| JP | 2006-109945 A | 4/2006 |
| JP | 2006-167403 A | 6/2006 |
| JP | 2007-144201 A | 6/2007 |
| JP | 2007-195980 A | 8/2007 |
| JP | 2007-195985 A | 8/2007 |
| JP | 2008-043789 A | 2/2008 |
| JP | 2008-259864 A | 10/2008 |
| WO | WO 93/015662 A1 | 8/1993 |
| WO | WO 97/010764 A1 | 3/1997 |
| WO | WO 99/040857 A1 | 8/1999 |
| WO | WO 01/012090 A1 | 2/2001 |
| WO | WO 2004/030553 A1 | 4/2004 |
| WO | WO 2004/032776 A1 | 4/2004 |
| WO | WO 2004/032777 A1 | 4/2004 |
| WO | WO 2004/082495 A1 | 9/2004 |
| WO | WO 2005/004735 A1 | 1/2005 |
| WO | WO 05/053785 A2 | 6/2005 |
| WO | WO 2006/119245 A2 | 11/2006 |
| WO | WO 2006/125558 A1 | 11/2006 |
| WO | WO 2007/044849 A1 | 4/2007 |
| WO | WO 2007/142601 A1 | 12/2007 |
| WO | WO 2008/147773 A1 | 12/2008 |
| WO | WO 2009/065140 A1 | 5/2009 |
| WO | WO 2012/110996 A2 | 8/2012 |
| WO | WO 2013/030349 A1 | 3/2013 |

OTHER PUBLICATIONS

European Patent Office, Extended European Search Report for European Application No. EP 22212171.7, dated Mar. 21, 2023, 7 pgs.
"New Products" Journal of Medical Engineering and Technology, vol. 19, No. 5 (Sep./Oct. 1995), pp. 189-190.
International Searching Authority/US, The International Search Report and the Written Opinion for International Application No. PCT/US09/39046 titled "Electrosurgical System", mailed Jul. 27, 2009.
International Preliminary Examining Authority/US, International Preliminary Report on Patentability for International Application No. PCT/US09/39046, titled "Electrosurgical System", dated Mar. 26, 2010.
European Patent Office, European Search Report for European Application No. EP 10 19 2593 dated Mar. 21, 2011, titled Electrosurgical System.
European Patent Office, European Search Report for European Application No. EP 10 19 2614 dated Apr. 18, 2011, titled Electrosurgical System.
European Patent Office, Extended European Search Report for European Application No. EP 10 19 2580 dated Jul. 21, 2011.
International Preliminary Examining Authority/US, International Preliminary Report on Patentability for International Application No. PCT/US09/39046, titled "Electrosurgical System", dated Jan. 17, 2012.
European Patent Office, The International Search Report and WrittenOpinion of the International Searching Authority for International Application No. PCT/US2011/054661, mailed Mar. 6, 2012.
U.S. Appl. No. 12/611,352, filed Nov. 3, 2009, titled Tissue Fusion/Welder Apparatus and Method.
U.S. Appl. No. 12/183,970 filed July 3 1, 2008, entitled Bipolar Electrosurgical Scissors.
U.S. Appl. No. 12/416,128, filed Mar. 31, 2009, entitled Electrosurgical System.
U.S. Appl. No. 12/416,668, filed Apr. 1, 2009, entitled Electrosurgical System.
U.S. Appl. No. 12/416,695, filed Apr. 1, 2009, entitled Electrosurgical System.
U.S. Appl. No. 12/416,765, filed Apr. 1, 2009, entitled Electrosurgical System.
The International Bureau of WIPO, The International Preliminary Report on Patentability for International Application No. PCT/US2011/054661, entitled Electrosurgical Instruments and Connections Thereto dated Apr. 2, 2013.
European Patent Office, European Search Report for European Application No. EP 13 17 4814.7 dated Sep. 30, 2013, titled Electrosurgical System.
International Searching Authority/US, The International Search Reportand the Written Opinion for International Application No. PCT/US2015/031452 titled "Electrosurgical Fusion Device", mailed Dec. 3, 2015.
Bertil Vallfors and Bjorn Bergdahl, Automatically controlled bipolar electrocoagulation—"COA-COMP," Neurosurg. Rev., 1984, pp. 187-190.
European Patent Office, European Search Report for European U.S. Appl. No. 12/151,288, dated Feb. 10, 2012, 8 pgs.
European Patent Office, Supplementary European Search Report for European U.S. Appl. No. 08/755,322, dated Apr. 18, 2012, 3 pgs.
European Patent Office, Supplementary European Search Report for European U.S. Appl. No. 08/755,322, dated Jun. 6, 2012, 2 pgs.
European Patent Office, European Search Report for European Patent Application No. EP 14199708.0, entitled "Electrosurgical System," dated Jul. 10, 2015, 14 pgs.
International Preliminary Examining Authority/US, International Preliminary Report on Patentability for International Application No. PCT/US2011/054661, titled "Electrosurgical Instruments and Connections Thereto", dated Apr. 2, 2013, 10 pgs.
International Searching Authority/US, The International Search Report and the Written Opinion for International Application No. PCT/US2015/066473, titled "Bipolar Electrosurgical Sealer and Divider," mailed Mar. 31, 2016, 13 pgs.
International Searching Authority/US, The International Search Report and the Written Opinion for International Application No. PCT/US15/033546, titled "Electrosurgical Seal and Dissection Systems," mailed Apr. 22, 2016, 31 pgs.
European Patent Office, Partial European Search Report for European Patent Application No. 15151398.3, dated Jun. 22, 2015, 9 pgs.
U.S. Appl. No. 12/416,751, filed Apr. 1, 2009, entitled Electrosurgical System, now U.S. Pat. No. 8,579,894 issued Nov. 12, 2013.
International Preliminary Examining Authority/US, International Preliminary Report on|Patentability for International Application No. PCT/US2015/031452, titled "Electrosurgical System," dated Dec. 1, 2016, 21 pgs.
International Preliminary Examining Authority/US, International Preliminary Report on Patentability for International Application No. PCT/US2015/033546, titled "Electrosurgical Laparoscopic Sealer and Dissector," dated Dec. 15, 2016, 22 pgs.
International Preliminary Examining Authority/US, International Preliminary Report on Patentability for International Application No. PCT/US2015/0066473, titled "Bipolar Electrosurgical Sealer and Divider," dated Jul. 6, 2017, 10 pgs.
European Patent Office, Extended European Search Report for European Application No. EP 17207793.5, dated Jun. 16, 2018, 9 pgs.
European Patent Office, Extended European Search Report for European Application No. EP 18165110.0, dated Jun. 13, 2018, 6 pgs.
International Searching Authority/US, The International Search Report and the Written Opinion for International Application No. PCT/US2019/049768 titled "Electrosurgical Generator Verification System." mailed Dec. 11, 2019, 19 pgs.

(56) References Cited

OTHER PUBLICATIONS

European Patent Office, Extended European Search Report for European Patent No. 19198318.8, entitled, "Bipolar Electrosurgical Sealer and Divider," dated Dec. 17, 2019, 10 pgs.
European Patent Office, Invitation to Pay Additional Fees for International Application No. PCT/US2019/049807, titled "Electrosurgical Generator Control System", mailed Dec. 19, 2019, 16 pgs.
International Searching Authority/US, The International Search Report and the Written Opinion for International Application No. PCT/US2019/049807 titled "Electrosurgical Generator Control System." mailed Feb. 12, 2020, 20 pgs.
International Searching Authority/US, The International Search Report and the Written Opinion for International Application No. PCT/US2019/059909 titled "Electrosurgical System," mailed Apr. 28, 2020, 23 pgs.
International Preliminary Examining Authority/US, International Preliminary Report on Patentability for International Application No. PCT/US2019/049768, titled "Electrosurgical Generator Verification System," dated Mar. 18, 2021, 13 pgs.
International Preliminary Examining Authority/US, International PreliminaryReport on Patentability for International Application No. PCT/US2019/049807, titled "Electrosurgical Generator Control System," dated Mar. 18, 2021, 13 pgs.
International Preliminary Examining Authority/US, International Preliminary Report on Patentability for International Application No. PCT/US2019/059909, titled "Electrosurgical System." dated May 27, 2021, 15 pgs.
European Patent Office, Extended European Search Report for European Application No. EP 23154961.9, dated May 22, 2023, 8 pgs.

\* cited by examiner

BIPOLAR ELECTROSURGICAL SEALER AND DIVIDER

CROSS-REFERENCE TO RELATED APPLICATIONS

This application is a continuation of U.S. patent application Ser. No. 16/578,070, filed Sep. 20, 2019 which is a continuation of U.S. patent application Ser. No. 14/973,366, filed Dec. 17, 2015 now U.S. Pat. No. 10,420,603 issued Sep. 24, 2019 which claims the benefit of U.S. Application No. 62/096,255, filed on Dec. 23, 2014, the entire disclosures of which are all hereby incorporated by reference as if set forth in full herein.

BACKGROUND

The present application relates generally to electrosurgical systems and methods and more particularly relates to a bipolar electrosurgical sealer and divider instruments, systems and methods.

Electrosurgical instruments or tools have become available that use electrical energy to perform certain surgical tasks. Typically, electrosurgical tools are hand tools such as graspers, scissors, tweezers, blades, needles, and other hand tools that include one or more electrodes that are configured to be supplied with electrical energy from an electrosurgical generator including a power supply. The electrical energy can be used to coagulate, fuse, or cut tissue to which it is applied.

Electrosurgical tools typically fall within two classifications: monopolar and bipolar. In monopolar tools, electrical energy of a certain polarity is supplied to one or more electrodes on the tool. A separate return electrode is electrically coupled to a patient. Monopolar electrosurgical tools can be useful in certain procedures, but can include a risk of certain types of patient injuries such as electrical burns often at least partially attributable to functioning of the return electrode. In bipolar electrosurgical tools, one or more electrodes is electrically coupled to a source of electrical energy of a first polarity and one or more other electrodes is electrically coupled to a source of electrical energy of a second polarity opposite the first polarity. Thus, bipolar electrosurgical tools, which operate without separate return electrodes, can deliver electrical signals to a focused tissue area with reduced risks.

Even with the relatively focused surgical effects of bipolar electrosurgical tools, however, surgical outcomes are often highly dependent on surgeon skill. For example, thermal tissue damage and necrosis can occur in instances where electrical energy is delivered for a relatively long duration or where a relatively high-powered electrical signal is delivered even for a short duration. The rate at which a tissue will achieve the desired coagulation or cutting effect upon the application of electrical energy varies based on the tissue type and can also vary based on pressure applied to the tissue by an electrosurgical tool. However, even for a highly experienced surgeon, it can be difficult for a surgeon to assess how quickly a mass of combined tissue types grasped in an electrosurgical instrument will be fused a desirable amount.

Attempts have been made to reduce the risk of tissue damage during electrosurgical procedures. For example, previous electrosurgical systems have included generators that monitor an ohmic resistance or tissue temperature during the electrosurgical procedure, and terminated electrical energy once a predetermined point was reached. However, these systems have had shortcomings in that they have not provided consistent results at determining tissue coagulation, fusion, or cutting endpoints for varied tissue types or combined tissue masses. These systems can also fail to provide consistent electrosurgical results among use of different tools having different tool and electrode geometries. Typically, even where the change is a relatively minor upgrade to tool geometry during a product's lifespan, the electrosurgical generator must be recalibrated for each tool type to be used, a costly, time consuming procedure which can undesirably remove an electrosurgical generator from service.

SUMMARY

In various embodiments, an electrosurgical instrument comprises lower and upper handles and lower and upper jaws. The lower handle has a proximal end and a distal end and an upper jaw is coupled to the distal end of the lower handle. The upper jaw has at least one electrode. The upper handle has a proximal end and a distal end and the lower jaw is coupled to the distal end of the lower handle. The upper jaw is pivotably connected to the lower jaw and a portion of the lower handle is arranged to decouple from the upper jaw when the upper and lower jaws are proximate each other in a closed position and in various embodiments only when the upper and lower handles are moved to a fuse position. In various embodiments, the instrument comprises a force and over compression regulation mechanism that is arranged such that a controlled force between the jaws is provided and in various embodiments is provided only when the handle or handles are moved to a fuse position.

In various embodiments, an electrosurgical instrument comprises lower and upper handles and lower and upper jaws. The lower handle has a lower handle housing connected to a jaw support joint and the upper jaw is connected to the jaw support joint. The upper jaw has at least one electrode. The lower handle and the upper jaw are movable relative the upper handle and the lower jaw. The lower jaw is coupled to a distal end of the upper handle. The jaw support joint is aligned with the upper jaw and the lower handle housing when the upper handle is spaced from the lower handle and the lower handle housing pivots or rocks relative to the jaw support joint when the upper and lower handles are proximate each other in a fuse position.

In various embodiments, an electrosurgical instrument is provided and comprises a lower handle comprising a support arm and a support spring connected to the support arm and an upper jaw connected to and extending from the lower handle, the upper jaw having at least one electrode. The instrument also comprises an upper handle and an lower jaw connected to and extending from the upper handle. The lower and upper handles are movable from a spaced position to a proximate position and the support spring is uncompressed when the upper and lower handles are in the proximate position. In various embodiments, the support spring is compressed and supplies a predetermined force to the upper and lower jaws through the support arm when RF energy is supplied to the at least one electrode.

These and other features of the invention will become more apparent with a discussion of embodiments in reference to the associated drawings.

BRIEF DESCRIPTION OF DRAWINGS

The present inventions may be understood by reference to the following description, taken in connection with the accompanying drawings in which the reference numerals designate like parts throughout the figures thereof.

DETAILED DESCRIPTION

Generally, an electrosurgical system is provided that includes an electrosurgical generator and an electrosurgical tool that are configured to optimally fuse tissue. The electrosurgical tool in accordance with various embodiments is provided to be used in open surgery with the ability to move, grasp and compress tissue and to deliver RF energy to fuse tissue. In accordance with various embodiments, the electrosurgical tool is a bipolar electrosurgical sealer and divider tool that is not insertable through a 5 mm-12 mm laparoscopic cannula but is typically used in open surgeries or through devices able to accommodate the non-cylindrical and larger than 12 mm distal end of the electrosurgical tool. RF energy is supplied by the electrosurgical generator configured to provide the appropriate RF energy to fuse tissue. The generator in accordance with various embodiments determines the appropriate RF energy and the appropriate manner to deliver the RF energy for the particular connected electrosurgical tool, the particular tissue in contact with the tool and/or a particular surgical procedure. In accordance with various embodiments, information or data to assist in the determination of the appropriate RF energy and manner to deliver the RF energy is supplied or obtained externally from the generator. The external source in various embodiments comprises one or more memory modules that may be included with the electrosurgical tool or via connections therebetween (wired or wireless) or via a separate tool, accessory, adapter and/or connections therebetween and/or via a separate port or connection to the generator. The generator retrieves and/or receives the data and utilizes the data to command or operate the generator to determine and supply the appropriate RF energy in the appropriate manner.

Figure 1:
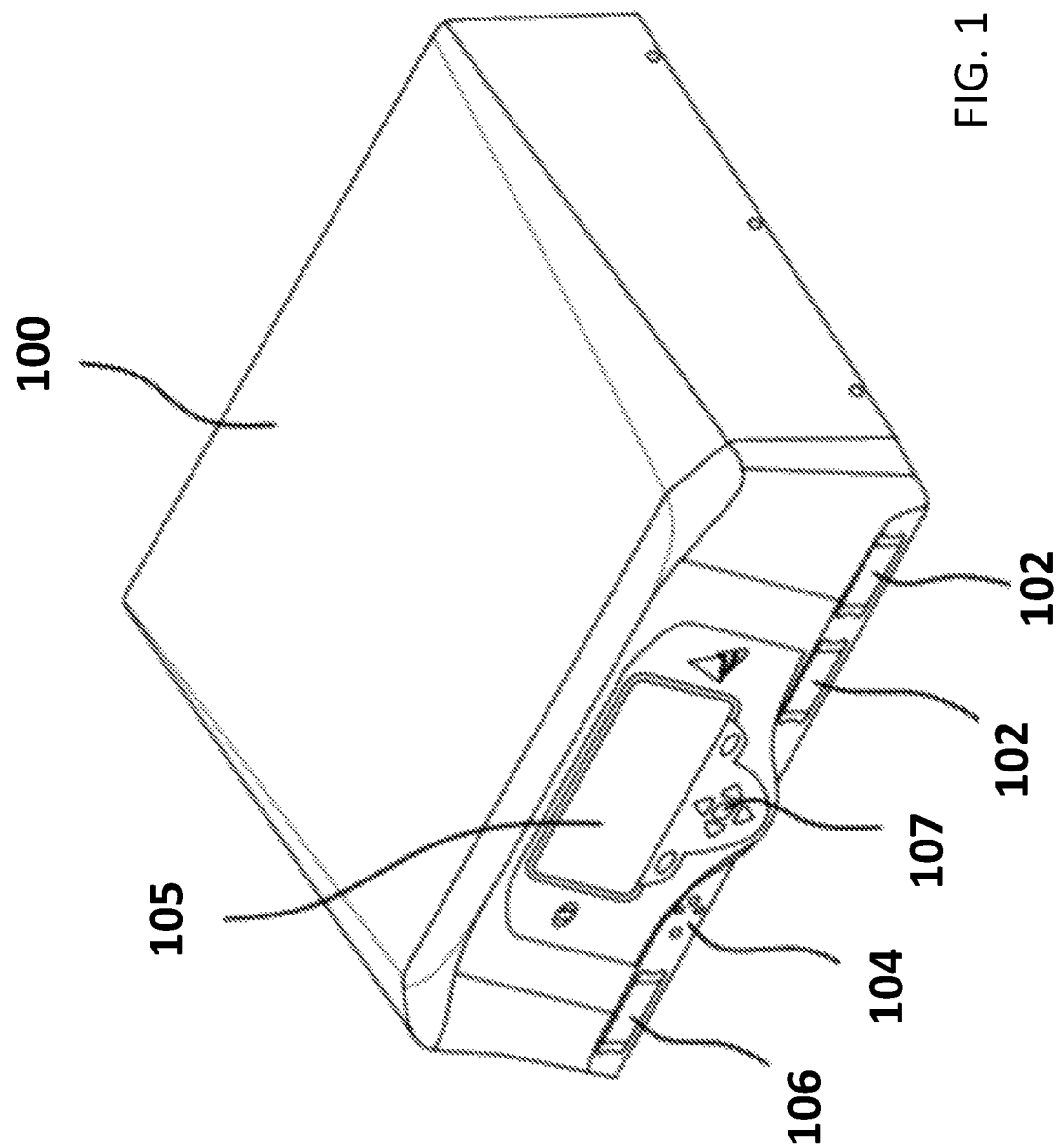
FIG. 1 is a perspective view of an electrosurgical generator in accordance with various embodiments of the present invention.
Figure 2:
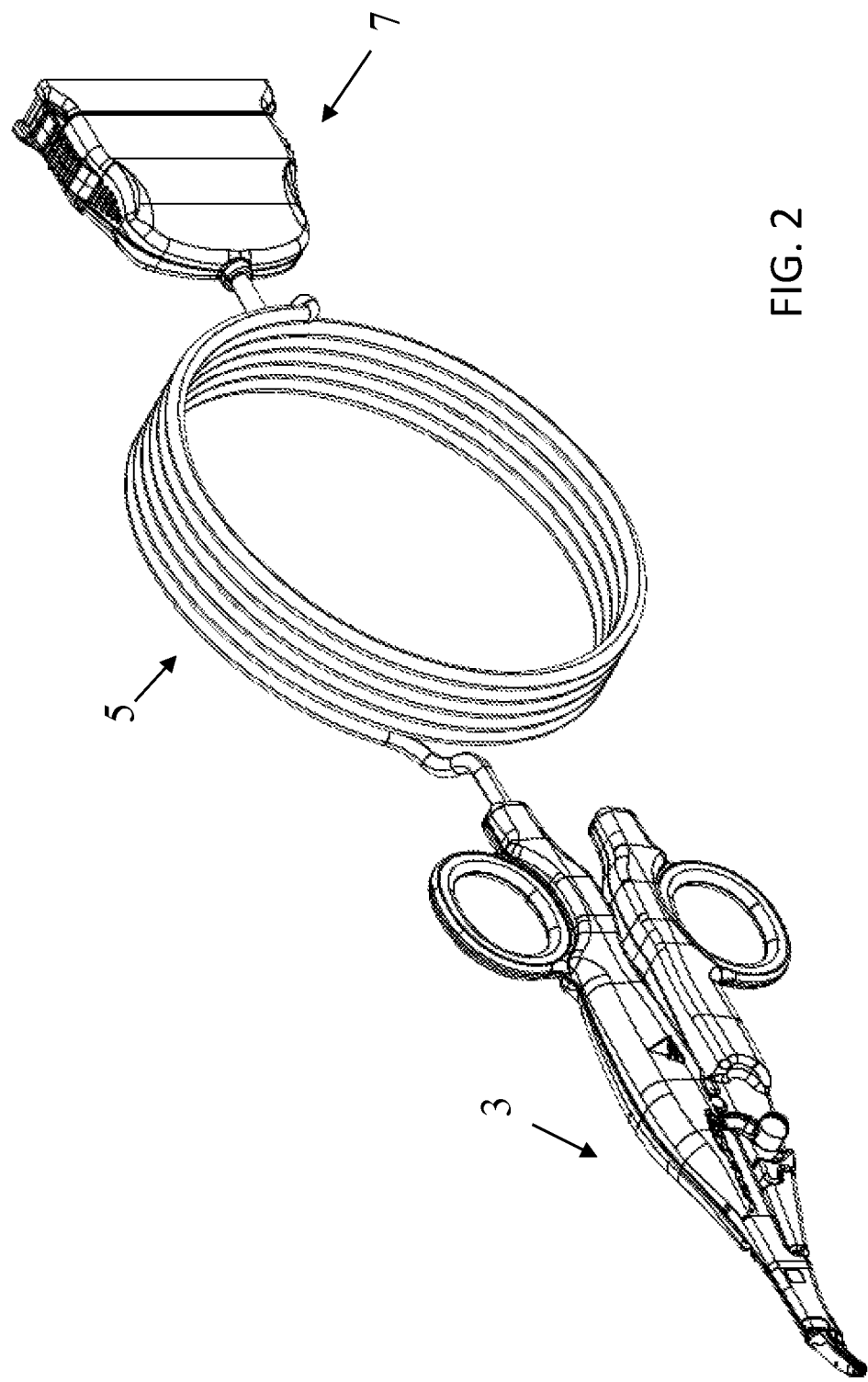
FIG. 2 is a perspective view of an electrosurgical fusion/sealer and dissector instrument in accordance with various embodiments of the present invention.
Figure 3:
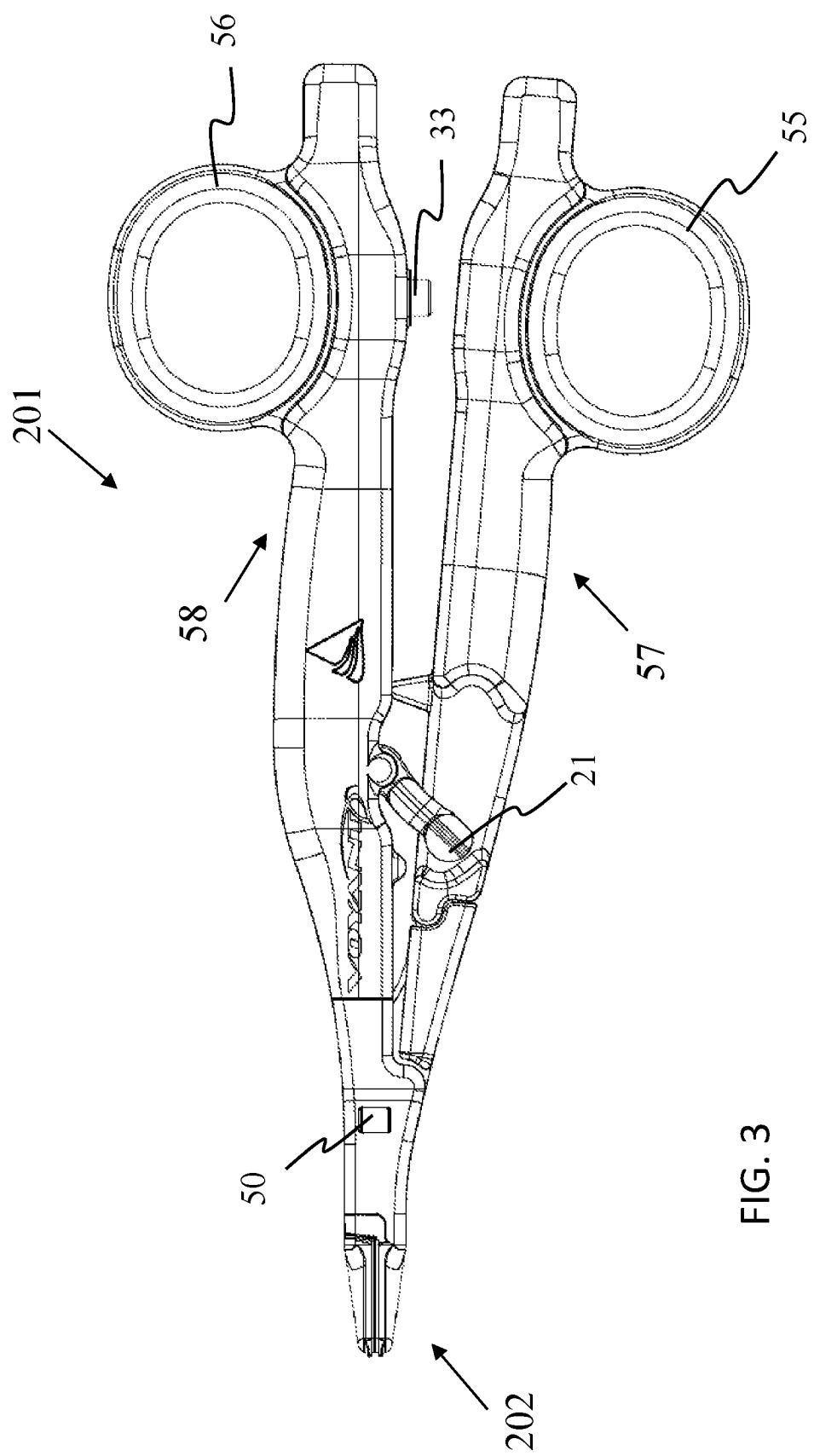
FIG. 3 is a side view of an electrosurgical fusion/sealer and dissector instrument in accordance with various embodiments of the present invention.
Figure 4:
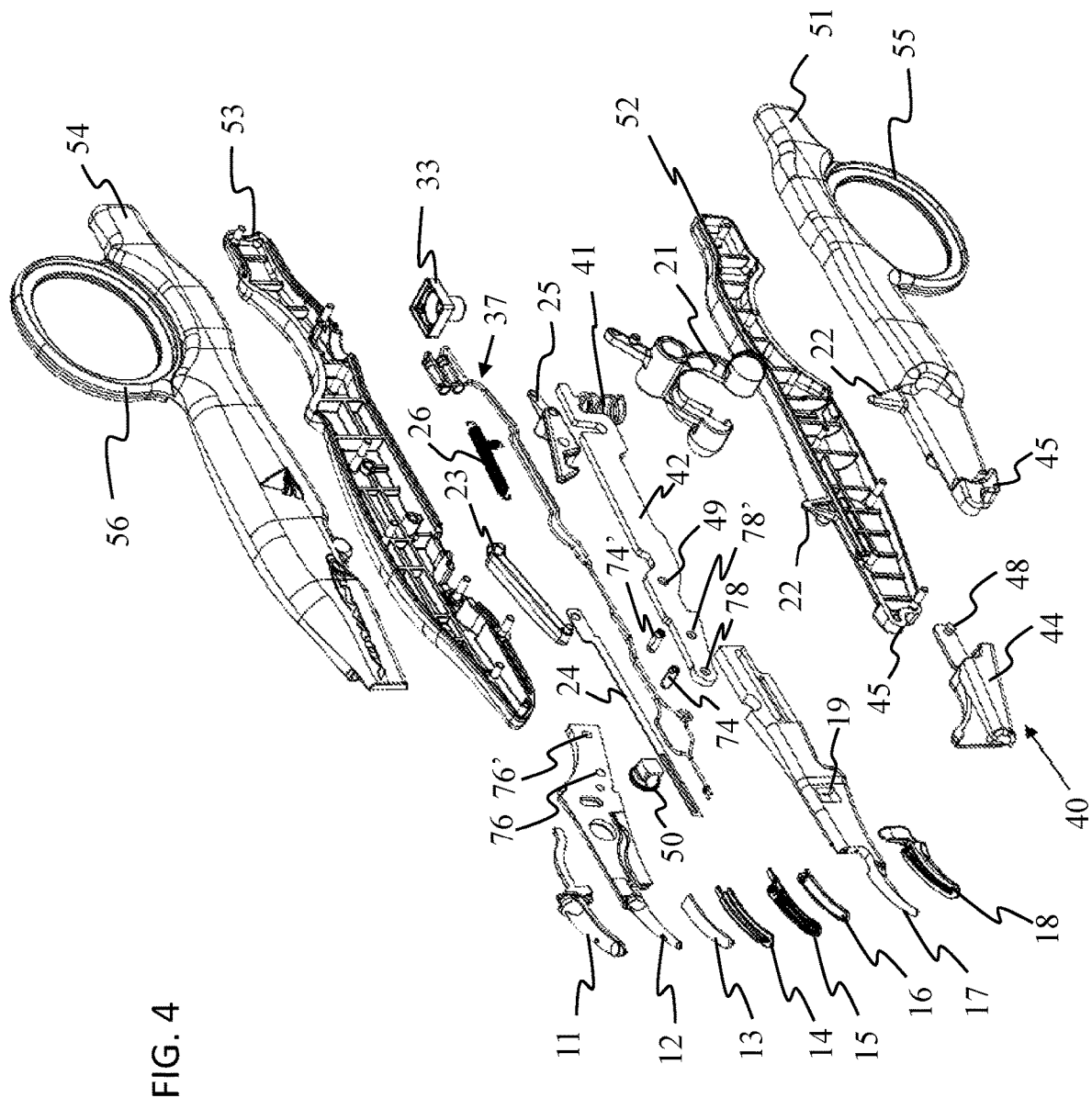
FIG. 4 is an exploded view of an electrosurgical fusion/sealer and dissector instrument in accordance with various embodiments of the present invention.
Figure 5:
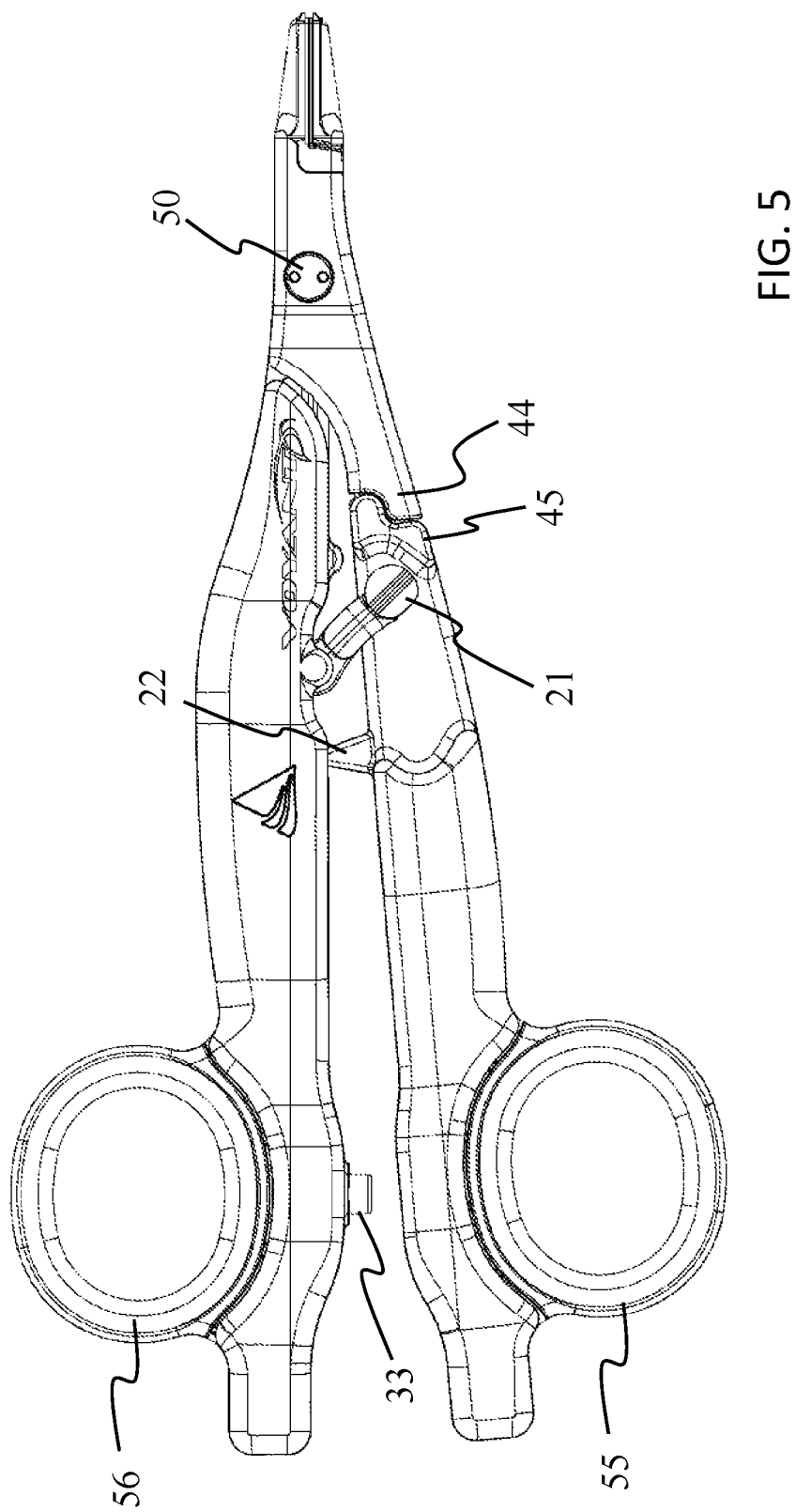
FIG. 5 is a perspective view of an electrosurgical fusion/sealer and dissector instrument in accordance with various embodiments of the present invention.
Figure 6:
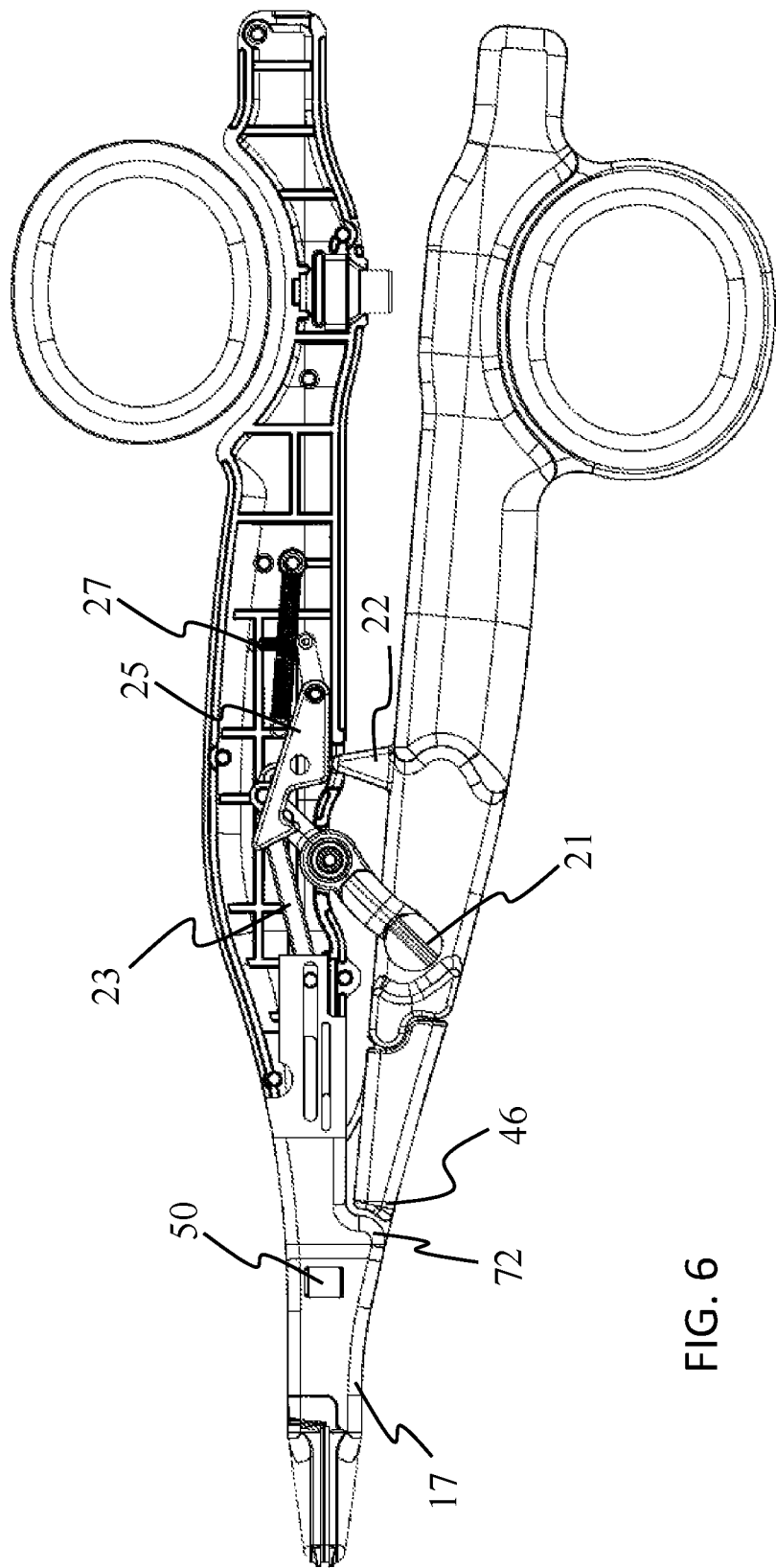
FIG. 6 is a side view of an electrosurgical fusion/sealer and dissector instrument in accordance with various embodiments of the present invention.

Referring to FIGS. 1-2, an exemplary embodiment of electrosurgical system is illustrated including an electrosurgical generator 100 and a removably connectable electrosurgical tool or instrument 3. The electrosurgical instrument 3 can be electrically coupled to the generator via a cabled connection 5 and tool plug or connector 7 to a tool port 102 on the generator. The electrosurgical instrument 3 may include audio, tactile and/or visual indicators to apprise a user of a particular predetermined status of the tool such as a start and/or end of a fusion operation. In other embodiments, the electrosurgical instrument can be reusable after sterilization and/or connectable to another electrosurgical generator for another surgical procedure. In some embodiments, a manual controller such as a hand or foot switch can be connectable to the generator and/or tool to allow predetermined selective control of the tool such as to commence a fusion operation.

In accordance with various embodiments, the electrosurgical generator 100 is configured to generate radiofrequency (RF) electrosurgical energy and to receive data or information from the electrosurgical instrument electrically coupled to the generator. The generator 100 in one embodiment outputs RF energy (e.g., 375 VA, 150V, 5 A at 350 kHz) and in one embodiment is configured to calculate a phase angle or difference between RF output voltage and RF output current during activation or supply of RF energy. The generator regulates voltage, current and/or power and monitors RF energy output (e.g., voltage, current, power and/or phase). In one embodiment, the generator 100 stops RF energy output under predefine conditions such as when a device switch is de-asserted (e.g., fuse button released), a time value is met, and/or active phase angle and/or change of phase is greater than or equal to a phase and/or change of phase stop value indicating end of an operation such as fusion of tissue between the jaws.

The electrosurgical generator 100 comprises two advanced bipolar tool ports 102, a standard bipolar tool port 106, and an electrical power port 104. In other embodiments, electrosurgical units can comprise different numbers of ports. For example, in some embodiments, an electrosurgical generator can comprise more or fewer than two advanced bipolar tool ports, more or fewer than the standard bipolar tool port, and more or fewer than the power port. In one embodiment, the electrosurgical generator comprises only two advanced bipolar tool ports.

Each advanced bipolar tool port 102 is configured to be coupled to electrosurgical instrument having an attached or integrated memory module. The standard bipolar tool port 106 is configured to receive a non-specialized bipolar electrosurgical tool that differs from the advanced bipolar electrosurgical instrument connectable to the advanced bipolar tool port 102. In one embodiment, the non-specialized bipolar electrosurgical tool does not include or is not connectable to a memory module that may have operational or parameter data for the operation of the tool. The electrical power port 104 is configured to receive or be connected to a direct current (DC) accessory device that differs from the non-specialized bipolar electrosurgical tool and the advanced electrosurgical instrument. The electrical power port 104 is configured to supply direct current voltage. For example, in some embodiments, the power port 104 can provide approximately 12 Volts DC. The power port 104 can be configured to power a surgical accessory, such as a respirator, pump, light, or another surgical accessory. Thus, in addition to replacing electrosurgical generator for standard or non-specialized bipolar tools, the electrosurgical generator can also replace a surgical accessory power supply. In some embodiments, replacing presently-existing generators and power supplies with the electrosurgical generator can reduce the amount of storage space required on storage racks carts or shelves and in the number of mains power cords required in a surgical workspace.

In one embodiment, connection of a non-specialized bipolar instrument into the standard bipolar port will not cause the generator to actively check the tool. However, the generator recognizes a connection so that the information of the non-specialized bipolar tool can be displayed. In accordance with various embodiments, the generator recognizes device connection status for each of the advanced tool ports 102 and authenticates connected devices before accepting RF energy activation requests (e.g., activation of a tool switch such as a fuse button). The generator in one embodiment reads authenticated data from the connected device and reads electrical control values (such as but not limited to voltage level settings, current level settings, power level settings, active phase angle level settings, RF energy output activation timing limits, tool short limits, tool open limits, tool model/identification, RF energy output line configurations, switch state command configurations and/or combinations thereof) from the authenticated and connected device.

In accordance with various embodiments, the electrosurgical generator 100 can comprise a display 105. The display can be configured to indicate the status of the electrosurgical system including, among other information, the status of the one or more electrosurgical tools and/or accessories, connectors or connections thereto. In some embodiments, the display can comprise a multi-line display capable of presenting text and graphical information such as for example an LCD panel display, which, in some embodiments can be illuminated via backlight or sidelight. In some embodiments, the display can comprise a multi-color display that can be configured to display information about a particular tool electrically coupled to the electrosurgical generator and a color that corresponds to a particular surgical procedure (such as, for example cutting operations displayed in yellow text and graphics, fusion or welding operations displayed in purple, and coagulation displayed in blue, bloodless dissection operations can be displayed in yellow and blue). In some embodiments, the display can be configured to simultaneously indicate status data for a plurality of tools electrically coupled to the electrosurgical generator and/or be portioned to display status information for each tool connected to a corresponding tool port. A visual indicator such as a status bar graph can be used to illustrate a proportion of total available electrical energy to be applied to the bipolar electrosurgical tool when actuated. In various embodiments, an electrosurgical tool operable to cut, coagulate, or fuse tissue could have three color-coded displays or bar graphs. In some embodiments, a user can toggle the display between presenting status of multiple electrically connected tools and status of a single electrically connected tool. In accordance with various embodiments, once a tool and/or accessory is connected and/or detected a window opens in the user interface display showing the type of tool connected and status.

The electrosurgical generator in accordance with various embodiments can comprise a user interface such as, for example a plurality of buttons 107. The buttons can allow user interaction with the electrosurgical generator such as, for example, requesting an increase or decrease in the RF energy supplied to one or more tools coupled to the electrosurgical generator. In other embodiments, the display 105 can be a touch screen display thus integrating data display and user interface functionalities. In accordance with various embodiments, through the user interface, the surgeon can set a voltage setting by the selection of one to three levels. For example, at level 1, voltage is set to 110V; at level 2, voltage is set to 100V; and at level 3, voltage is set to 90V. Current is set to 5 Amps and power is set to 300 VA for all three levels. In other embodiments, the voltage is preset or defaults to a specific level such as level 2. In other embodiments, like the current and power settings, the voltage setting is not user adjustable to simplify operation of the generator and as such a predetermined default voltage setting is utilized, e.g., voltage is set to 100V.

In one embodiment, the electrosurgical instrument can further comprise one or more memory modules. In some embodiments, the memory comprises operational data concerning the tool and/or other tools. For example, in some embodiments, the operational data may include information regarding electrode configuration/reconfiguration, the tool uses, operational time, voltage, power, phase and/or current settings, and/or particular operational states, conditions, scripts, processes or procedures. In one embodiment, the generator initiate reads and/or writes to the memory module.

In one embodiment, each advanced bipolar electrosurgical tool comes with a memory module and/or an integrated circuit that provides tool authentication, configuration, expiration, and logging. Connection of such tools into the receptacles or ports initiates a tool verification and identification process. Tool authentication in one embodiment is provided via a challenge-response scheme and/or a stored secret key also shared by the generator. Other parameters have hash keys for integrity checks. Usages are logged to the generator and/or to the tool integrated circuit and/or memory. Errors in one embodiment can result in unlogged usage. In one embodiment, the log record is set in binary and interpreted with offline tools or via the generator.

In one embodiment, the generator uses time measurement components to monitor a tool's expiration. Such components utilize polling oscillators or timers or real-time calendar clocks that are configured at boot time. Timer interrupts are handled by the generator and can be used by scripts for timeout events. Logging also utilizes timers or counters to timestamp logged events.

In accordance with various embodiments, the generator provides the capability to read the phase difference between the voltage and current of the RF energy sent to the connected electrosurgical tool while RF energy is active.

While tissue is being fused, phase readings are used to detect different states during the fusion process.

In one embodiment, the generator logs usage details in an internal log that is down loadable. The generator has memory for storage of code and machine performance. The generator also has reprogrammable memory that contains instructions for specific tool performance. The memory for example retains a serial number and tool use parameters. The generator may also store information on the type of tools connected. Such information includes but is not limited to a tool identifier, e.g., a serial number of a connected tool, along with a time stamp, number of uses or duration of use of the connected tool, power setting of each and changes made to the default setting. The memory in one embodiment holds data for about two months or about 10,000 tool uses and is configured to overwrite itself as needed.

The generator in accordance with various embodiments does not monitor or control current, power or impedance. The generator regulates voltage and can adjust voltage. Electrosurgical power delivered is a function of applied voltage, current and tissue impedance. The generator through the regulation of voltage can affect the electrosurgical power being delivered. However, by increasing or decreasing voltage, delivered electrosurgical power does not necessarily increase or decrease. Power reactions are caused by the power interacting with the tissue or the state of the tissue without any control by a generator other than by the generator supplying power.

The generator once it starts to deliver electrosurgical energy does so continuously until a fault occurs or a specific phase parameter is reached. In one example, the jaws of the electrosurgical tool can be opened and thus compression relieved at any time before, during and after the application of electrosurgical energy. The generator in one embodiment also does not pause or wait a particular duration or a predetermined time delay to commence termination of the electrosurgical energy.

With reference also to FIGS. 3-15, in accordance with various embodiments, an electrosurgical instrument is provided. In the illustrated embodiment, the instrument includes an actuator 201 coupled to or from which jaws 202 extend. In one embodiment, the actuator 201 includes two finger loops 55, 56 each extending from a different handle 57, 58 with both handles movable relative to each other. Both handles are pivotally coupled together through a central or main pivot 50. In operation, the handles are manipulated by a user, e.g., a surgeon, to move the jaws, selectively opening and closing the jaws.

Figure 13:
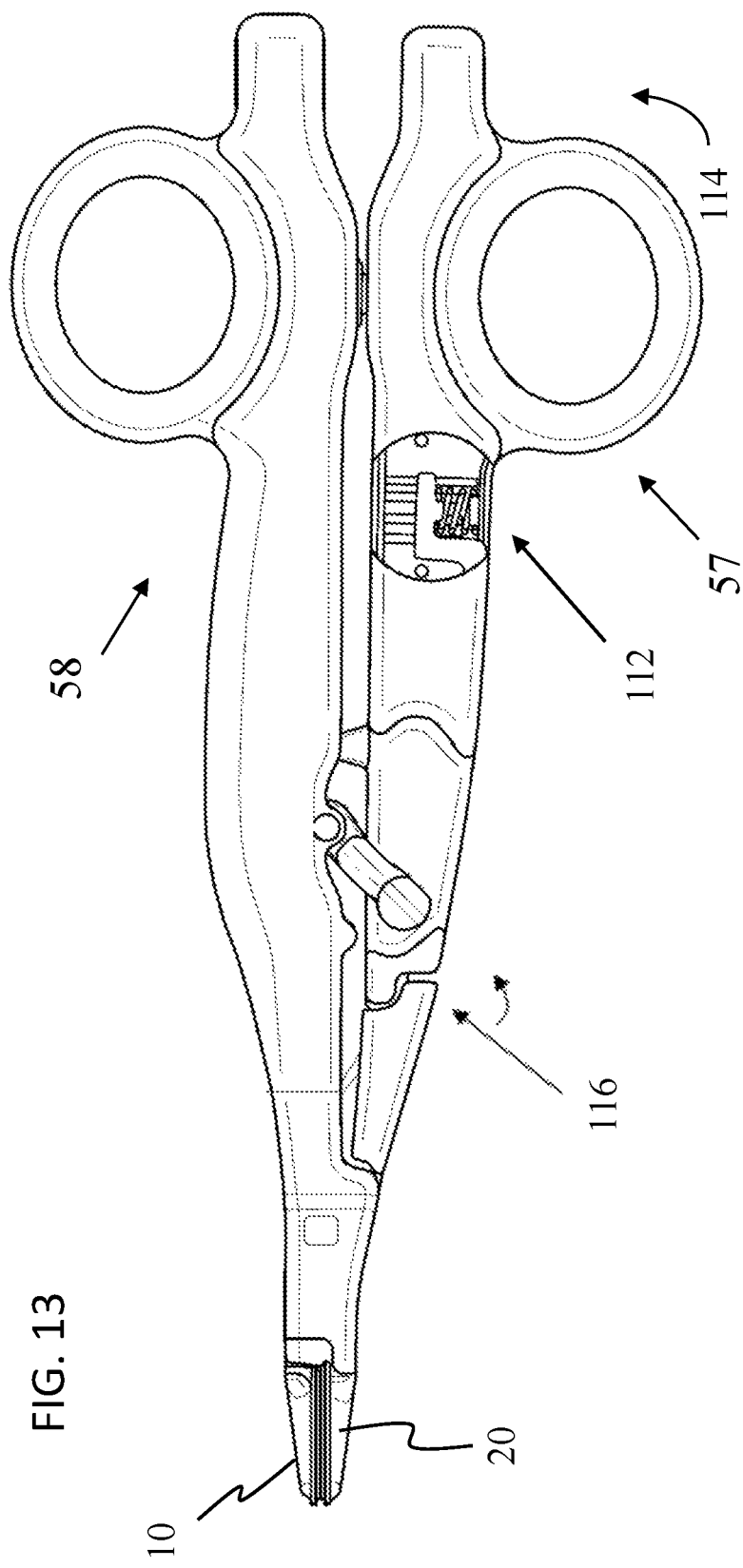
FIG. 13 is a side view of an electrosurgical fusion/sealer and dissector instrument in accordance with various embodiments of the present invention.

A fuse/seal switch or button 33 is activated upon complete closure of the handles as shown in at least FIG. 13 and indicated by arrow D. The fuse button 33 can, but is not operationally pushed by a surgeon. In operation, the jaws are arranged to be fully closed grasping and compressing tissue between the jaws while the seal button 33 remains inactivated. The handles are closed further at which time a force regulation and over-compression or spring arm mechanism, as will be described in greater detail below, ensures a predetermined compression force or range of compression forces is applied or at most applied on the tissue between the jaws. Once the handles are fully closed, first or lower handle 57 or an outer surface of portion of handle 57 engages the fuse button 33. As such, as the handle 57 moves proximate to the other opposing handle, second or upper handle 58, while the jaws still remain fully closed, the seal button 33 between the handles is depressed. Upper handle 58, in one embodiment, comprises of upper handle housing 53, 54 that forms a cavity in which portions of the fuse button are captured within. In one embodiment, the fuse button has a first state indicating contact or providing tactile indication (such as increased friction, force or resistance), visual and/or audio indications to a surgeon that the button has been contacted and a second state with similar indications that indicate the button has been fully depressed and thus fusion of tissue between the jaws have been activated or started and thus RF energy is being applied to the tissue. Once the fuse button is activated, associated circuitry or contacts are connected to connect appropriate electrodes of the jaws with associated connections of the generator to supply RF energy to fuse tissue grasped between the jaws.

In various embodiments, the instrument comprises a translatable mechanical cutting blade that is coupled to a blade actuator, such as, blade trigger or lever 21 of the actuator 201. The mechanical cutting blade is actuated by the blade lever 21 to divide tissue between the jaws. A blade lock hook 25 within one of the handles prevents movement of the blade lever 21 but upon closure of the handles/jaws the blade lock hook releases the blade lever 21. The blade hook when engaged by a blade unlock projection 22 in the other handle releases the blade lever allowing the blade lever to be moved and thus to actuate the blade through the jaws and the tissue grasped between the jaws.

The main or central pivot 50 about which the handles and jaws pivot has an opening through which a blade slider 24 is extendable and retractable there through and thus the pivot 50 does not hinder or restrict the blade slider regardless of the position of the pivot. In one embodiment, the main pivot 50 has a circular end inserted and connected to a circular opening in an upper or second jaw support 12 and a square, rectangular or non-circular end inserted and connected to a square, rectangular or non-circular opening 19 in a lower or first jaw support 17. The circular connection between the central pivot 50 and the upper jaw support 12 allows the upper jaw support to pivot about the central pivot. Conversely, the square or non-arcuate connection between the central pivot 50 and the lower jaw support 17 resists rotation or pivoting of the lower jaw support about the central pivot 50. Accordingly, in one embodiment, the upper or second jaw moves from a proximate position to a spaced position and vice versa relative to the non-movable or relatively stationary lower jaw as the lower handle is moved towards the upper handle rotating about the central pivot 50.

The blade slider 24 is connected to a blade lever arm 23. The blade lever arm 23 is connected to the blade trigger 21. In one embodiment, a projection such as a pin extends from a distal portion of the blade lever arm 23 into an opening in a proximal end of the blade slider 24 connecting the components together. In one embodiment, a projection extends from a proximal portion of the blade lever arm 23 into an opening in one end of the blade trigger 21 connecting the components together. The other end of the blade trigger 21 is exposed and accessible by the user with the blade trigger being pivotable about a trigger pivot at or near the mid-point of the blade trigger. As such, as the blade trigger is pulled or rotated by the user proximally or counter-clockwise, the end of the blade trigger 21 connected to the blade lever arm 23 moves distally which simultaneously moves the blade lever arm distally. The blade lever arm 23 connected to the blade slider 24 slides or moves the blade slider distally. Integrated with or attached to a distal end of the blade slider is a cutting blade, knife or cutting edge or surface. As such, as the blade slider 24 translates longitudinally through a channel in the jaws, tissue grasped between the jaws is cut. In one embodiment, the cutting edge or surface is angled to facilitate cutting of the tissue between the jaws. In various embodiments, the cutting blade is a curved blade, a hook, a knife, or other cutting elements that is sized and configured to cut tissue between the jaws.

A spring 26 connected to the blade trigger 21 biases the blade trigger back proximally and thus when the blade trigger is released by the surgeon, the blade trigger rotates or pivots back to its initial position. In one embodiment, a spring 27 is connected to the blade lever arm that biases the blade lever arm and the blade slider connected thereto back to the initial or retracted position. Hence, once the blade trigger is released, the blade slider translates longitudinally back proximally through the channel in the jaws to its initial position. Upon return, the blade trigger engages the blade lock hook 25 moving or lifting the hook as the trigger continues to proceed back to its initial or starting position. Once back to the initial position, the blade hook is free to move back and engage the trigger holding it in place if not obstructed by the unlock projection 22.

In one embodiment, the lower jaw support 17 includes a guide channel that is dimensioned to receive and support the blade slider 24 to ensure alignment and support longitudinal translation of the slider distally and/or proximally. In one embodiment the lower jaw support includes a pin channel at a proximal end of the lower jaw support away from the lower jaw or distal end of the instrument. The proximal pin channel is dimensioned to receive and support the pin or connection between the blade slider 24 and the blade lever arm 23 as the pin, blade slider and the blade lever arm translates distally and proximally and to align and support longitudinal translation of the slider and pin distally and/or proximally.

The jaws are opened and closed by corresponding movements of the handles or handle connected to a respective jaw. The jaws and handles are movable through at least three states, conditions or positions. In a first or initial (or open) position, the jaws are opened with the upper and lower jaws spaced from each other and the handles are open with the upper and lower handles being spaced from each other. In a second (or clamped) position, the jaws are closed with the upper and lower jaws proximate to each other and the handles are closed with the upper and lower handles being proximate to each other. In a third (or fuse) position, the jaws remain closed as in the second position but the handles are fully closed with the upper and lower handles having portions that contact or interact with each other (e.g., a fuse button contacted or activated). The handles and jaws are movable between each of the three positions. The jaws, when closed upon tissue, apply pressure or compression to the tissue between the jaws. This compression corresponds to the closure force being applied by the surgeon. In accordance with various embodiments, the instrument includes a force regulation and over-compression or spring arm mechanism that applies the proper compression while not over squeezing or applying too much compression due to differences in operational use and/or size variations of the tissue. In various embodiments, the force regulation and over compression mechanism is or is only activated or operates when the jaws and/or handles are moved from the second position to the third position.

In accordance with various embodiments, the instrument applies a predetermined pressure or range of pressures by allowing one of the device handles to control the clamping pressure through an internal support spring 41. As the two handle close together and bottoms out, one handle is able to dislocate or decouple rotationally from the jaws and a rocking motion is introduced. The rocking motion in one embodiment is the result of the handle 57, jaw support joint 40 and mating contours 44, 45 interacting with each other. As the handle and in particular the handle housing dislocates or decouples from the jaws and in particular the support joint, the internal spring 41 compresses which subjects a jaw support arm 42 to a controller moment when the jaws are fully closed. With the support spring controlling the clamping pressure instead of a fixed rigid lever, for example, the instrument is able to maintain and ensure a particular clamping pressure range. Additionally, any further pressure or movement by the handles as applied by the surgeon is removed or decoupled from the jaws. As such, the handle is dislocated or decoupled rotationally from the jaws which allows the handles to move to a fully closed or fuse position without creating additional surface pressure load or compression on the tissue/vessel.

Figures 14A, 14B:
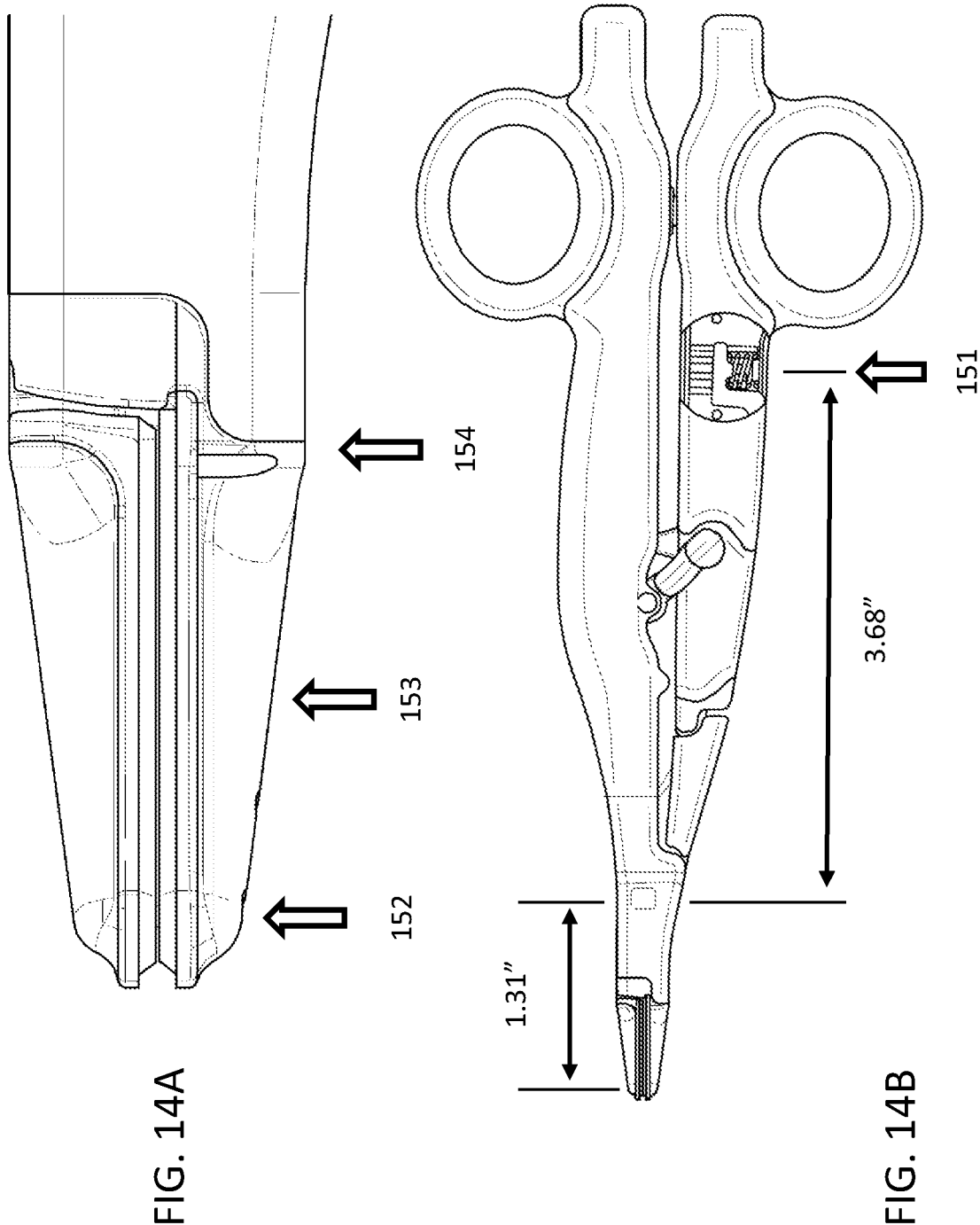
FIG. 14A is a side view of a distal end of an electrosurgical fusion/sealer and dissector instrument in accordance with various embodiments of the present invention.
FIG. 14B is a side view of an electrosurgical fusion/sealer and dissector instrument in accordance with various embodiments of the present invention.
Figure 15:
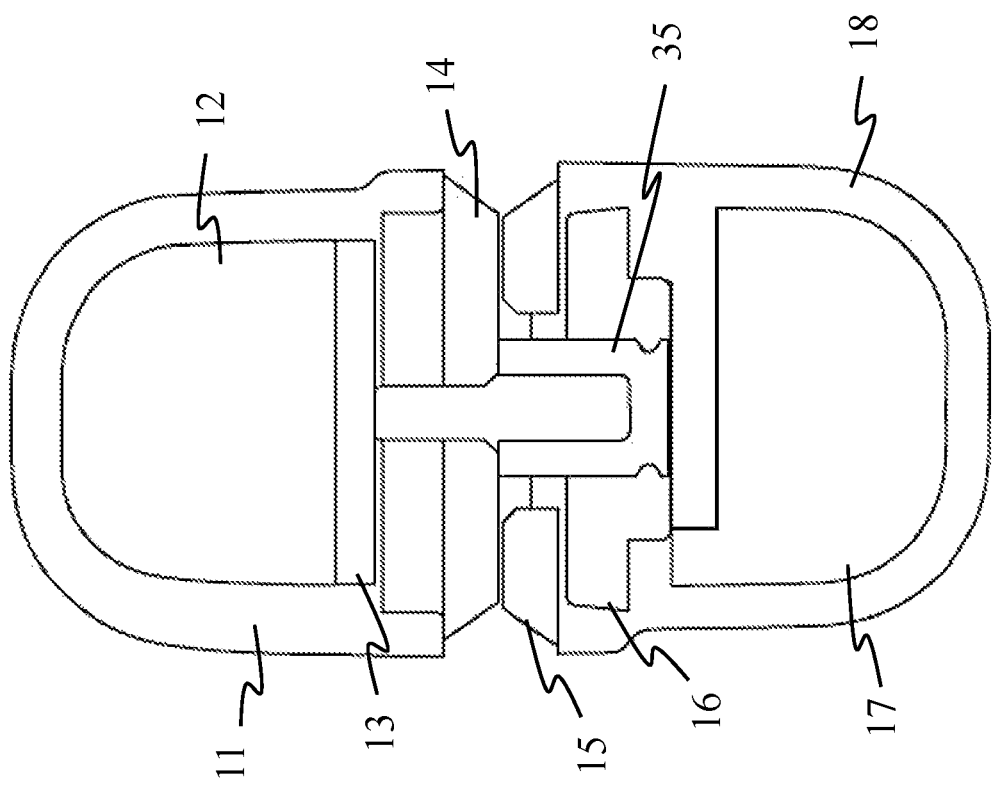
FIG. 15 is a cross sectional view of an electrosurgical fusion/sealer and dissector instrument in accordance with various embodiments of the present invention.

The support spring 41 supplies the set pressure or force that allows the instrument to target or set a predetermined optimal sealing pressure as shown in FIGS. 14A-B. In particular, a spring applying 2 pounds of force on the support arm when the handles bottom out (arrow 151) applies a range of pressure of 6 lbs. (arrow 152) to 10.5 lbs. (arrow 154) at the jaws with about 7.5 lbs. (arrow 153) at the jaws' midpoint. Likewise, a spring applying 3.25 pounds of force on the support arm when the handles bottom out (arrow 151) applies a range of pressure of 9.25 lbs. (arrow 152) to 16 lbs. (arrow 154) at the jaws with about 12 lbs. (arrow 153) at the jaws' midpoint. The distance between the spring and the pivot 50 (e.g., 3.68 inches) and the distance between the pivot 50 and the end of the jaws or sealing surface (e.g., 1.31 inches) remain constant. As such, the controlled forces applied by the instrument vary along the length of the jaws from about 5.5 pounds of force near the distal tip or portion in various embodiments to about 16 pounds of force near the proximal portion of the jaws in various embodiments. In accordance with various embodiments, a force ratio from the jaw arm to the jaw tip is a ratio of 2.81:1. The spring 41 is also not exposed or accessible by the surgeon and thus prevents potential interference with a surgeon's operation, catching on a surgeon's gloves, misalignment, interference and/or harm to the mechanism, and increases ease of assembly and manufacture.

Figure 7:
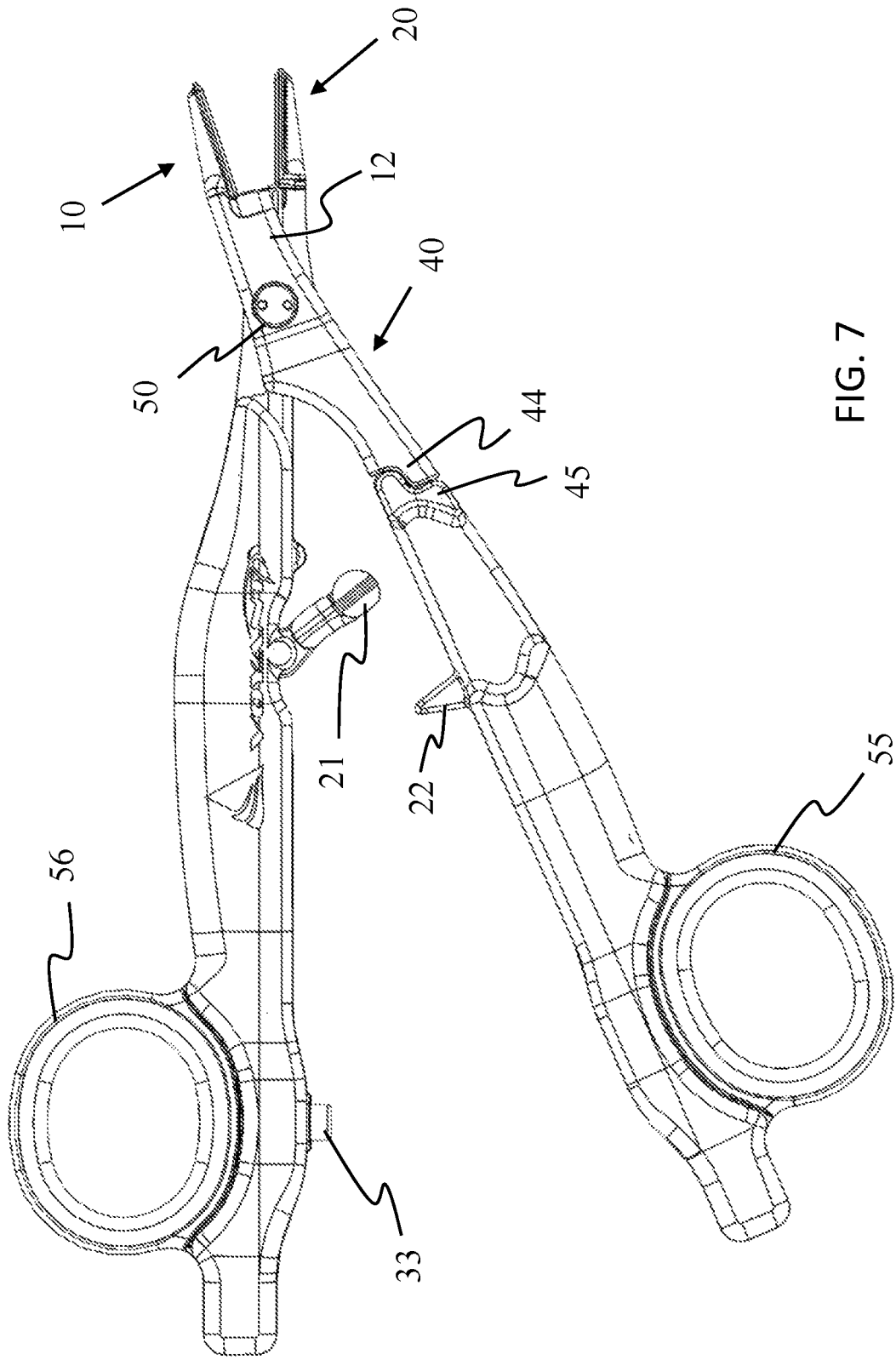
FIG. 7 is a side view of an electrosurgical fusion/sealer and dissector instrument in accordance with various embodiments of the present invention.
Figure 8:
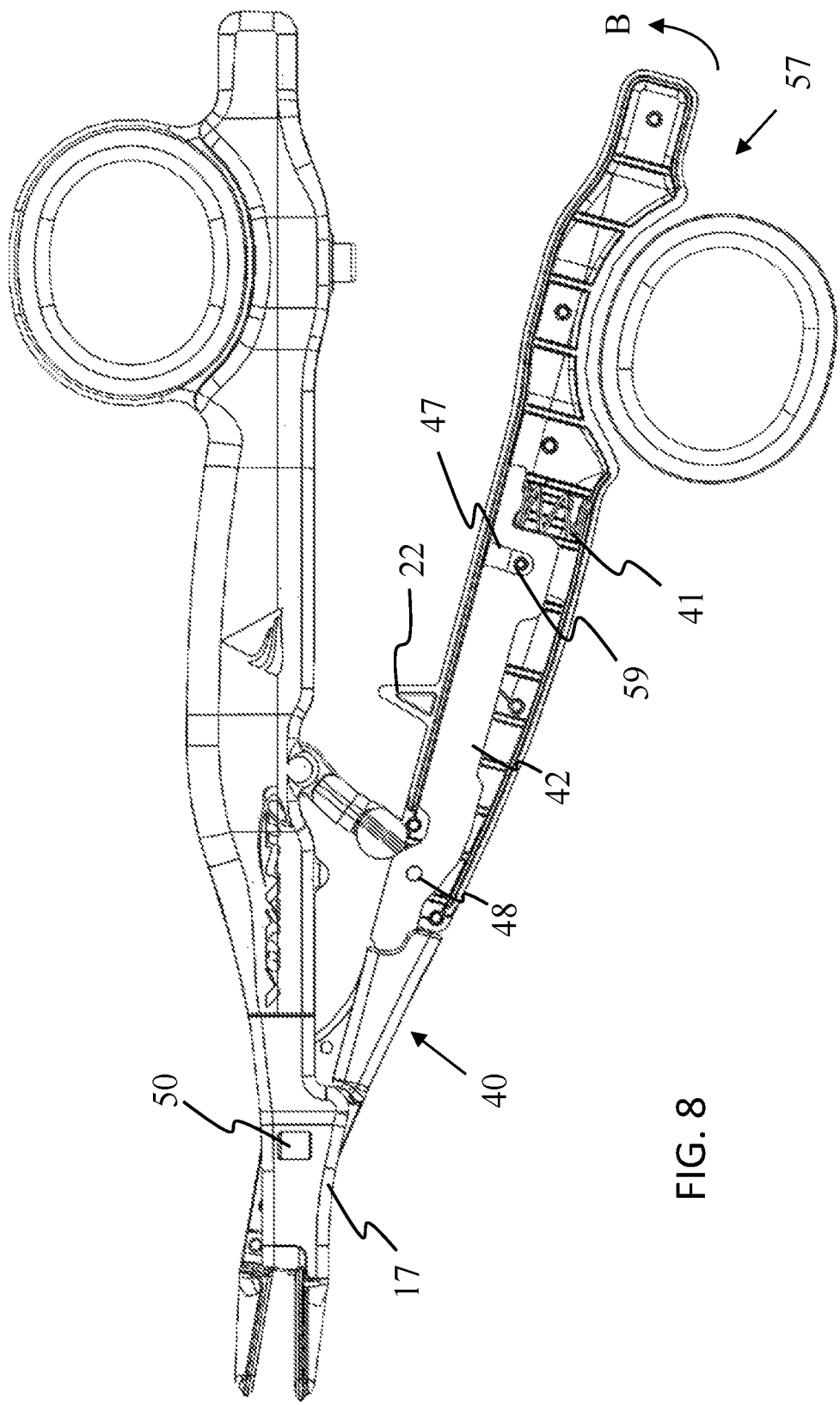
FIG. 8 is a side view of an electrosurgical fusion/sealer and dissector instrument in accordance with various embodiments of the present invention.
Figure 9:
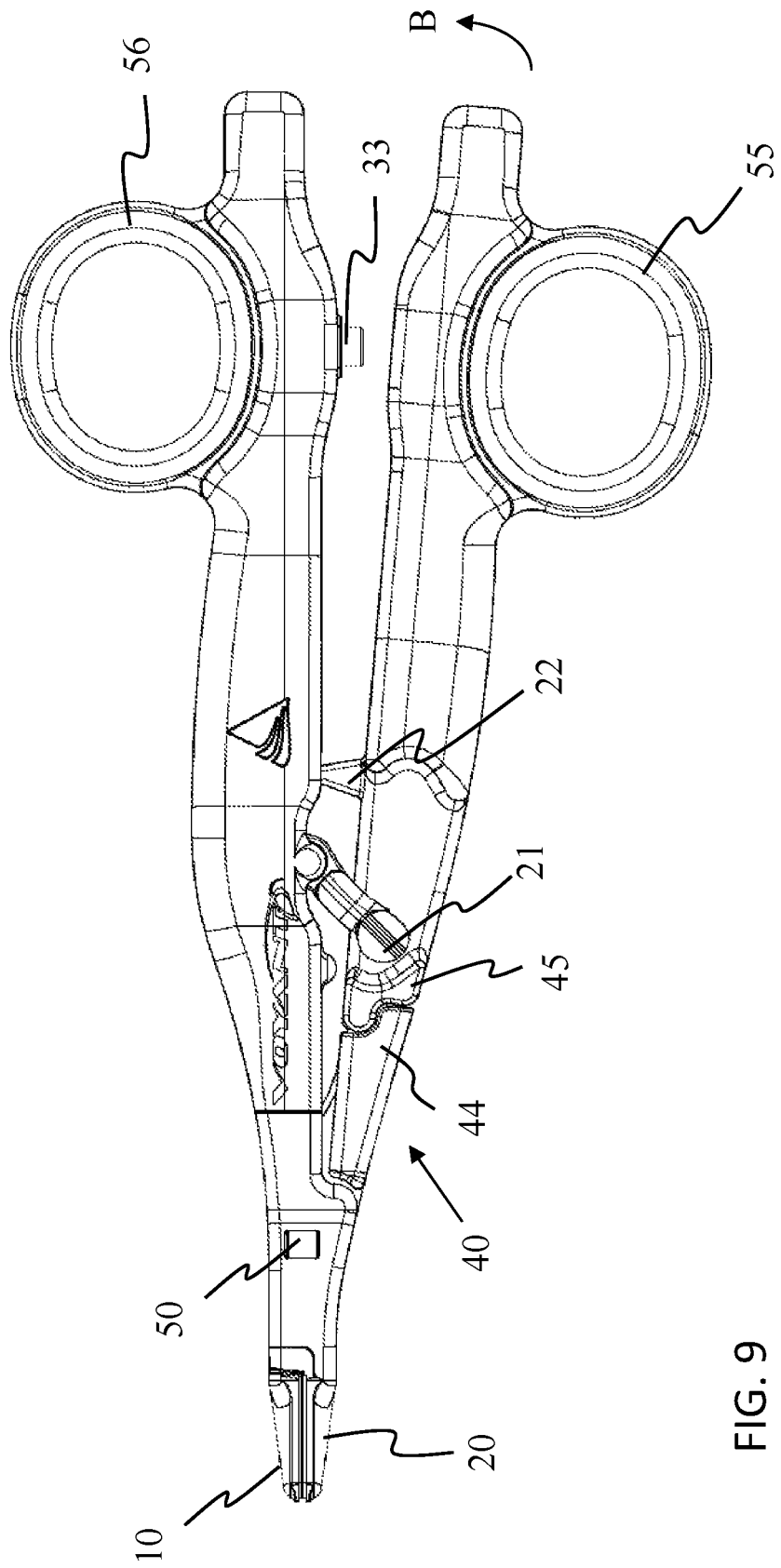
FIG. 9 is a side view of an electrosurgical fusion/sealer and dissector instrument in accordance with various embodiments of the present invention.
Figure 10:
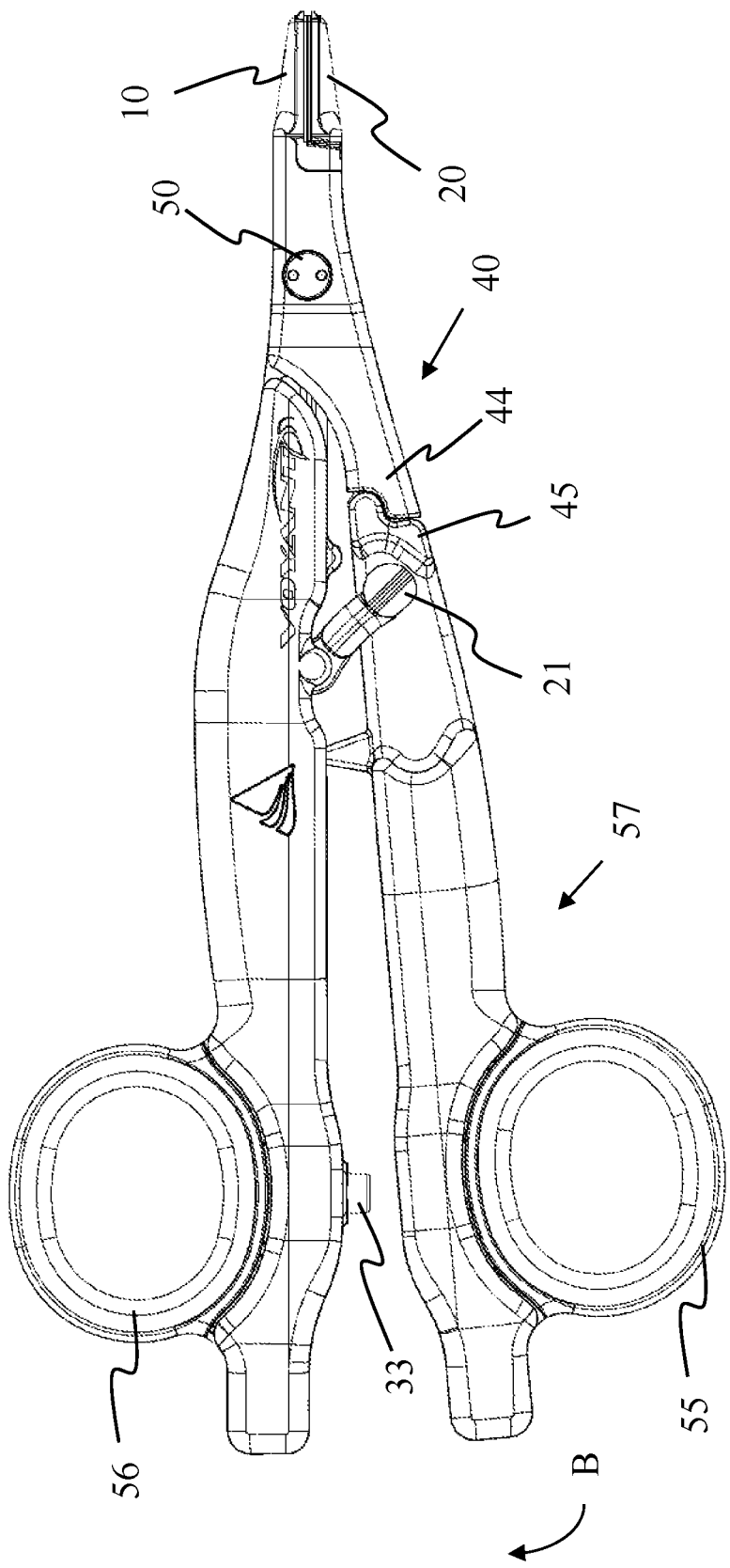
FIG. 10 is a side view of an electrosurgical fusion/sealer and dissector instrument in accordance with various embodiments of the present invention.
Figure 11:
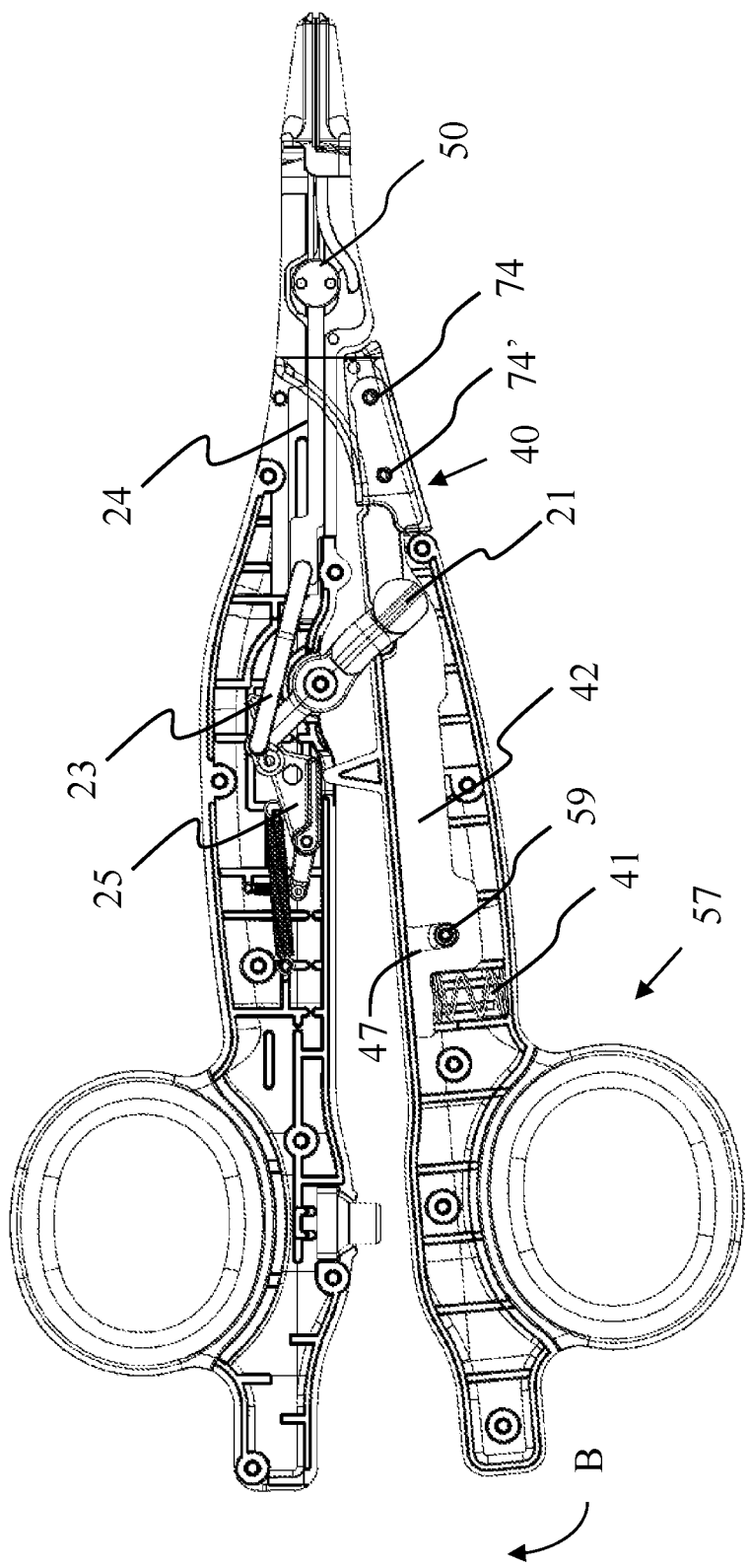
FIG. 11 is a side view of an electrosurgical fusion/sealer and dissector instrument in accordance with various embodiments of the present invention.
Figure 12:
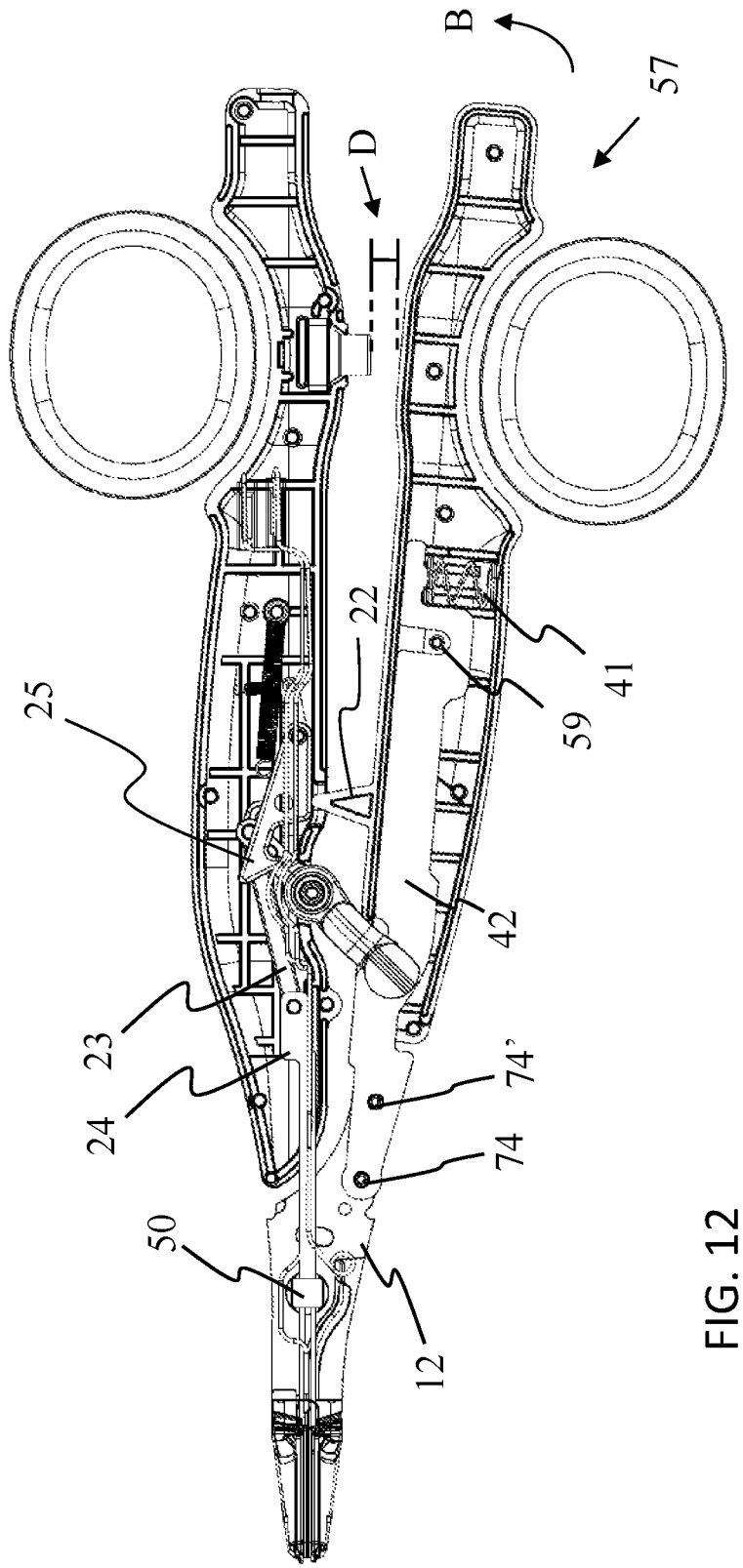
FIG. 12 is a side view of an electrosurgical fusion/sealer and dissector instrument in accordance with various embodiments of the present invention.

In accordance with various embodiments, a surgeon can open and close the jaws (upper and lower jaws 10, 20) of the electrosurgical instrument to move and grasp tissue there between. Once the surgeon grasps tissue to be sealed and/or cut, the surgeon will continue to rotate and close the handles to unlock the blade lever and engage the fuse button 33 (FIG. 7). Additionally, further movement of the lower or bottom handle 57 in the rotational direction indicated by the arrow B causes the housing of the bottom handle 57 to decouple or break away from the jaw support joint 40. Corresponding mating curved surfaces or contours 44, 45 provides external support to assist in the decoupling of the housing of the bottom handle from the jaw support joint 40 and facilitate or introduce a rocking motion between the jaw support joint 40 and the lower handle 57. In various embodiments, the jaw support joint has a curved cutout 46 that mates with a curved surface 72 of the lower jaw support to further facilitate the rocking motion and/or the pivoting of the handles relative to each other.

The pivot or jaw support arm 42 is connected to the lower or bottom handle 57. The bottom handle 57 defines an enclosed cavity and in one embodiment the bottom handle 57 comprises lower left and right handle housing 51, 52 that define the enclosed cavity therebetween. Near the proximal end of the jaw support arm 42 is the support spring or biasing member 41. A slot 47 is also formed near the proximal end of the jaw support arm 42 and the support spring 41 is connected to the proximal end of the jaw support arm 42 near the slot. The spring and slot are enclosed in the cavity of the bottom handle 57. The spring and slot extends along parallel axes and are perpendicular or traverse to the longitudinal axis of the instrument (e.g., an axis through which the blade extends and retracts) and/or the jaw support arm 42. A pin 59 extending from within the bottom handle 57 extends through the slot or channel 47 in the jaw support arm. In one embodiment, from an initial or open position to a close position in which the jaws are open and closed respectively, the pin is near the bottom or closed end of the slot and the spring 41 remains uncompressed. As the handles are fully closed, bottomed out and moved to a third fuse position, the pin 59 of the handle moves from the bottom end of the slot towards the upper end of the slot and the spring 41 compresses. At the distal end of the jaw support arm 42, the jaw support arm is connected to the upper jaw support 12 via projections, such as pins or posts 74.

In accordance with various embodiments, the jaw support joint 40 includes a cavity in which a distal portion of the jaw support arm 42 is received and connected to the jaw support joint 40. In one embodiment, one or more pins 74 extend through apertures 78 at the distal end of the jaw support arm and into receptacles or openings in the jaw support joint to secure the jaw support arm 42 to the jaw support joint 40. In one embodiment, the one or more pins 74 also extend through apertures 76 at the proximal end of the upper jaw support 12 securing the upper jaw support 12 to the jaw support joint 40 and the support arm 42.

The jaw support joint 40 in one embodiment at the proximal end or portion is a projection or post 48 that extends into an opening 49 in the jaw support arm 42 thereby further connecting the jaw support joint to the jaw support arm. The opening in the jaw support arm is between the proximal and distal end of the support arm. A portion of the proximal end of the jaw support joint also extends into the handle housings 51, 52 thereby capturing and securing the jaw support joint to the handle 57. The jaw support arm 42 connected to the jaw support joint 40 remains fixed and thus further pivoting or rotational movement of the jaw support arm 42 is prevented even though the bottom handle may continue to rotate under pressure of the user further closing the handles together. As the bottom handle 57 continues to rotate after the jaws are closed, the support spring 41 is compressed (arrow 112) by the interaction of the jaw support arm 42 being fixed and the bottom handle 57 rotating or moving (arrow 114).

When the handles bottom out, the support spring 41 inside the lower handle applies a specific force on the jaw support arm 42 which translates to a specific or controlled clamping force at the jaws. The lower handle housing breaking away from the jaw support arm 42 disassociates or dislocates (arrow 116) any additional compression applied by the user through the squeezing of the handles together. At the dislocation or decoupling operational point, in accordance with various embodiments, the internal support spring 41 is engaged or activated. As such, prior to that dislocation operational point the spring is not engaged and thus the surgeon can open and close the jaws and grasp or dissect different tissue to seal, reposition or move out of the way without having to overcome a spring force with each movement. This reduces or prevents hand fatigue. Also, potential trauma to tissue not intended to be fused is avoided through the unintended application of force by the instrument for merely grasping or moving tissue. In one embodiment, the support spring 41 provides or supplies the only clamping force at the jaws with force supplied by the surgeon's squeezing of the handles being dissociated or decoupled from the jaws.

The jaws include upper and lower jaws with both jaws having an electrode or conductive pad. The conductive pad 14 of the upper jaw and the conductive pad 15 of the lower jaw are electrically coupled to the electrosurgical generator via wires and connectors 37 to supply RF energy to tissue grasped between the conductive pads. The conductive pads are arranged to have opposing polarity. The upper jaw includes an upper jaw support 12 with an assembly spacer 13 positioned between the upper jaw support 12 and the conductive pad 14. The upper jaw also includes an overmold 11 or is overmolded. The lower jaw includes a lower jaw support 17 with an assembly spacer 16 positioned between the jaw support 17 and the conductive pad 15.

In various embodiments, a blade channel extends longitudinally along the length of the upper jaw, the lower jaw or both through which the blade operationally traverses. The lower jaw also includes an overmold 18 or is overmolded. Surrounding a portion of the blade channel is one or more conductive posts 35. The conductive posts assist in strengthening the blade channel and support the tissue to be cut. The conductive posts also assist in ensuring the tissue being cut adjacent or proximate to the blade channel is fused as the conductive posts also participate in the transmission of RF energy to the tissue grasped between the jaws.

In one embodiment, wires and associated connections 37 extend from the fuse switch or button 33 through the upper housing, upper and lower jaw supports to the respective upper and lower jaws and the respective connections to the upper and lower electrodes. The actuator in one embodiment comprises a wire harness that includes insulated individual electrical wires or leads contained within a single sheath. The wire harness can exit the handle with the button and forms part of the cabled connection 5. The wires within the harness can provide electrical communication between the instrument and the electrosurgical generator and/or accessories thereof. In one aspect, once activated, the fuse button completes a circuit by electrically coupling at least two leads together. As such, an electrical path is then established from an electrosurgical generator to the actuator to supply RF energy to the instrument.

In some embodiments, electrode geometry on the conductive pads of the jaw assembly ensures that the sealing area completely encloses the distal portion of the cutting path. In accordance with various embodiments, the dimensions of the jaw surfaces are such that it is appropriately proportioned with regards to the optimal pressure applied to the tissue between the jaws for the potential force the force mechanism can create. Its surface area is also electrically significant with regards to the surface area contacting the tissue. This proportion of the surface area and the thickness of the tissue have been optimized with respect to its relationship to the electrical relative properties of the tissue. As such, in various embodiments, the conductive pads are flat and planar and are operationally arranged to transmit RF energy between the pads and through tissue between the pads with the RF energy supplied by an electrosurgical generator to optimize fusing of tissue therebetween. Also, in various embodiments, the total surface area of the conductive pad of the upper jaw is larger than the total surface area of the conductive pad of the lower jaw to optimize fusing and dissecting of tissue therebetween.

In accordance with various embodiments, an electrosurgical system can include an electrosurgical generator and an electrosurgical tool. The electrosurgical tool is used in open procedures where the ligation and division of vessels and tissue bundles are desired. The electrosurgical tool fuses vessels by delivering radio frequency (RF) energy to tissue captured between the jaws of the device and subsequently or simultaneously cuts the sealed tissue with the use of a user-actuated blade. The generator can provide an electrosurgery endpoint by determining the phase end point of a tissue to be treated. The electrosurgical system can include more than one electrosurgical tool for different electrosurgical operations and can include a variety of user interface features and audio/visual performance indicators. The electrosurgical system can also power conventional bipolar electrosurgical tools and direct current surgical appliances.

Turning now to some of the operational aspects of the electrosurgical tool or instrument described herein in accordance with various embodiments, once a vessel or tissue bundle has been identified for fusing, the first and second jaws are placed around the tissue. The handles are squeezed together and thereby pivot the first jaw towards the second jaw effectively clamping the tissue. The actuator 201 has a first or initial position in which the jaws 202 are in an open position and in one embodiment the first and second jaws opening defines about a 30 degree angle.

The force applied to the tissue by the jaws is translated through the support arm on one of the actuation handles. Once the preloaded force has been overcome, the support arm will begin to move closer to the opposite handle. When the engaged fuse position is reached and a small, e.g., minimum, amount of tissue is between the jaws the support spring ensures that the force applied to the electrodes of the jaws is near the lower end of the force range required for optimal vessel sealing. When a large, e.g., maximum, amount of tissue is placed in the jaws, the rocker arm spring ensures that the maximum amount of force applied does not exceed the maximum end of the force range used for optimal vessel sealing.

As such, the force and over compression regulation mechanism provides a minimum force, optimal for sealing vessels and tissue, that is maintained regardless of the amount of substance contained between the upper and lower jaws. This mechanism also reduces the risk that an extremely large amount of force is applied to the tissue. If too much force is applied to a vessel or tissue bundle, potential damage could occur. Thus, if a very small vessel or thin tissue bundle is clamped within the jaw, the instrument applies the minimum amount of force required to obtain a good tissue weld. The same is true with a very large vessel or tissue bundle. Since the travel of the jaw can vary greatly depending on tissue thickness, the force applied by the jaw is adjustable. The instrument is self-adjusting and automatic (no action from the user). The force and over compression regulation mechanism provides the self-adjustment, applying a specific range of force along the length of the electrode.

The continued manipulation of the handles pivots the handles to a location where the movable handle causes the depression of the fuse button. The depression of the fuse button causes the application of the radio frequency energy to the tissue between the jaws. Once the tissue has been fused and/or cut, the actuator is reopened by moving the handles apart. To cut tissue between the jaws, the user can actuate the blade trigger 21. When the blade trigger is moved proximally, the blade lever pivots, forcing the cutting blade distally. The cutting blade thus advances forward and divides the tissue. When the surgeon releases the blade trigger, the blade spring resets the cutting blade to its original position.

In accordance with various embodiments, the actuator 201 has a cutting or fuse position in which the jaws 202 are in a closed position and the blade trigger has been depressed advancing the cutting blade to its distal most position. In various embodiments, the blade trigger may be activated to cut tissue between the jaws and/or the fuse button or switch may be activated to fuse tissue between the jaws.

As described, in accordance with various embodiments, the instrument 3 has a first state in which the jaws 201 are spaced from each other and thus the handles 202 are also spaced from each other. The instrument is thus positioned to grasp tissue between the jaws. In the second state of the instrument, the jaws are proximate to each other to grasp tissue between the jaws and likewise the handles are proximate to each other. No RF energy is applied to the tissue. The surgeon can revert back to the first state by opening the jaws and thus positioning the jaws again to grasp the tissue or other tissue. In the third state of the instrument, the handles are moved further and closer to each other. However, the jaws remain in the same position as in the second state and thus over-compression of the tissue is avoided. Movement to the third state is needed to activate the switch or button to thereby apply RF energy to the tissue grasped between the jaws. Also, movement to the third state, releases the blade lock hook and thereby tissue grasped between the jaws can be cut through the activation of the blade lever. Movement to the third state also reduces the potential of unintentionally releasing the tissue. Also, inadvertent cutting of tissue or along the wrong tissue lines are avoided. Additionally, this state allows the application of constant and continuous predefined compression or range of compression on the tissue between the jaws before, during and after the activation of the RF energy, thereby enhancing the sealing or fusion of the tissue between the jaws.

In various embodiments, the lower handle pivoted and spaced away from the upper handle in an open position or first state defines an open distance between the lower handle and the upper handle and the lower handle proximate the upper handle in a closed position or second state defines a closed distance between the lower handle and the upper handle, the closed distance (D) being smaller than the open distance. In various embodiments, the lower handle proximate the upper handle in the fuse position defines a fuse distance between the lower handle and the upper handle, the fuse distance being smaller than the closed distance. In accordance with various embodiments, the fuse distance corresponds to or is greater than the height of the uncompressed support spring or the distance between the proximal end of the support arm and the lower handle housing.

Figure 16:
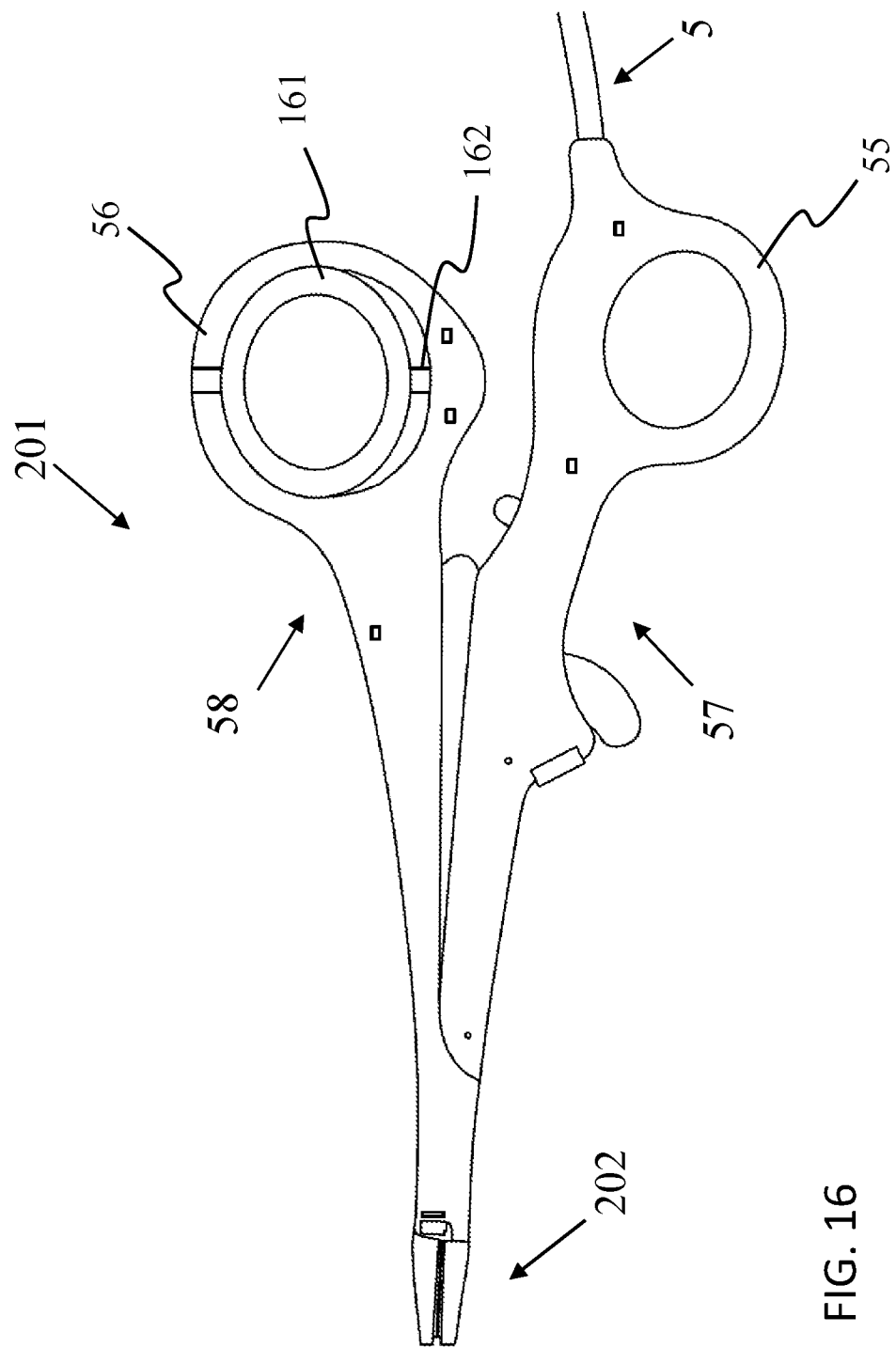
FIG. 16 is a side view of an electrosurgical instrument in accordance with various embodiments of the present invention.

In reference to FIG. 16, in one embodiment, the upper handle 58 connected to the lower jaw 20 includes an upper ring handle or finger loop 56 and the lower handle 57 connected to the upper jaw 10 includes a lower ring handle or finger loop 55. In one embodiment the upper ring handle includes an internal loop 161 biased by a spring 162. The internal loop is spring loaded to the upper ring handle and moves vertically or perpendicular to the longitudinal axis. The spring applies a specific force to the upper handle to control the clamping force at the jaws. As such, over compression of the tissue and thus unintended tissue trauma is prevented. In one embodiment, the spring comes into play only when the jaws are closed. It is appreciated however that the internal loop can operationally not engaged by the surgeon for example grasping the outer portion of the ring handle or handle. As such, the internal loop would not be engaged and thus the clamping force would not be regulated by the spring connected to the loop. In various embodiments, a fuse button is disposed between the internal loop and the ring handle and thus in order to fuse tissue grasped between the jaws, the internal loop is engaged thereby engaging the spring. Various other components and/or combinations thereof are also applicable to the illustrated embodiment in FIG. 16 and vice versa.

In accordance with various embodiments, the gripping force generated between the jaws can vary along the length of the jaws from a relative maximum near the proximal end to a relative minimum near the distal end. The electrosurgical instrument is configured such that the forces are optimized along the length of the electrode portions of the jaws such that a predetermined force range for vessel sealing is maintained. A predetermined maximum amount of force utilized to obtain a proper vessel seal is not exceeded at the proximal end of the active electrodes (closest to the pivot). In addition, a gripping force at the distal most ends of the electrodes is greater than a predetermined minimum amount of force for optimal vessel sealing. The gripping force generated at every point along the jaws is within the range defined by the predetermined maximum force and the predetermined minimum force to achieve optimal sealing.

It should also be appreciated that springs are described throughout the description for ease of description. However, other biasing mechanisms could be used such as elastic bands, hydraulics, etc. It should be appreciated that the force and over compression mechanism avoids spring configurations such as springs or biasing mechanisms toward or near the proximal end of the handles and exposed or biased between both handles that causes a back force requiring a surgeon to overcome to close the handles and thus the jaws. Thus, with a surgeon performing multiple seals, such as twenty to fifty seals, in a single surgical procedure, hand fatigue can set in as the biasing mechanism would be sufficiently strong to ensure compression of the tissue at the jaws and also prevent a surgeon from over compressing the tissue. Additionally, a predetermined force or range a forces would also be difficult to control and predict given the different operational force and varying force that can be applied by a surgeon and various surgeons for different surgical procedures over varying time frames. Furthermore, interference with a surgeon's hand or operation may also occur if the bias mechanism is exposed near the proximal end of the instrument. Springs or bias mechanisms disposed near or within the jaws of the instrument can cause interference with tissue disposed or attempted to be grasped by the jaws and cause misalignment or non-parallel jaw closures which thereby may cause improper tissue sealing or cutting. Additionally, eschar or other types of buildup on the jaws may interfere with such bias mechanisms. Furthermore, placement of such biasing mechanisms may cause an increase in jaw size and thus potentially obstruct a surgeon's view of the fusion site or potentially interfere with the blade mechanism.

In one aspect, the determination of the end-point of the fusion process is given by monitoring the phase shift of voltage and current during the fusion process. In accordance with various embodiments, the application of RF energy via an electrosurgical generator in conjunction with the measuring or monitoring of phase shift are provided to fuse vessels and tissue in accordance with various embodiments of electrosurgical system. As such, the instrument generating the seal, fusion or connection of the tissue provides atraumatic contact to the connecting tissue and provides enough burst pressure, tensile strength, or breaking strength within the tissue.

In one embodiment, the generator initially determines the initial instrument impedance and/or capacitance (e.g., during plug-in of the instrument connector to the electrosurgical generator), where tolerances/changes in the instrument characteristics are then accounted for in the tissue measurement and endpoint determination process. This can allow for tissue measurement values which are independent of the ohmic and capacitive values and/or tolerances of a specific electrosurgical instrument.

Exemplary RF energy control process for the electrosurgical generator and associated electrosurgical instrument for fusing or sealing tissue in accordance with various embodiments is provided in which RF energy is supplied by the generator through the connected electrosurgical instrument or tool. The generator monitors at least the phase and/or change of phase of the supplied RF energy. In various embodiments, if a phase crossing or polarity change from positive to negative or negative to positive is encountered, a phase stop is determined. The phase stop in various embodiments includes a predefined phase angle and/or change of phase angle that indicates an optimal tissue seal or fusion endpoint and/or is based on a determined tissue property such as size, permittivity, conductivity and/or applied voltage, current and/or power. The generator continues to monitor at least the phase and/or change of phase of the supplied RF energy. If the phase stop is reached or exceeded, the process is done or termination procedures are initiated and/or RF energy supplied by the generator is stopped.

In accordance with various embodiments, at a detected phase crossing or polarity change, the generator identifies the voltage level of the supplied RF energy and, depending on the determined voltage level a specific course of action is selected. For example, if the identified voltage is less than 50 volts, the voltage level is set to a constant value of 25 volts and the RF energy continues to be supplied until the monitored phase angle reaches a phase angle end point value of −7 degrees. If the identified voltage is greater than or equal to 50 volts but less than or equal to 60 volts, the voltage level is held constant at the identified voltage and RF energy continues to be supplied until the monitored phase angle reaches a phase angle end point value of −14 degrees. If the identified voltage is greater than 60 volts, the voltage level is held constant at the identified voltage and RF energy continues to be supplied until the sensed phase angle reaches a phase angle end point value of −14.5 degrees.

In certain embodiments, an electrosurgical fusion/sealer and divider tool comprises a handle assembly, a jaw assembly, and a force and over compression regulation mechanism. The handle assembly comprises two pivotably movable handles. The jaw assembly comprises a first jaw and a second jaw. The first jaw has an inner surface, an outer surface, and at least one electrode disposed on the inner surface. The second jaw has an inner surface, an outer surface, and at least one electrode disposed on the inner surface. The jaw assembly is actuatable by movement of the handle assembly from an open configuration in which the inner surface of the first jaw is spaced apart from the inner surface of the second jaw to a closed configuration in which the inner surface of the first jaw is proximate the inner surface of the second jaw. The force and over compression regulation mechanism is configured such that in the closed configuration, the jaw assembly delivers a gripping force between the first jaw and the second jaw between a predetermined minimum force and a predetermined maximum force.

In other embodiments, the jaw assembly comprises a blade. The blade is longitudinally advanceable along the inner surface of the first jaw along a cutting path defined between a retracted position adjacent the proximal end and an advanced position between the proximal end and the distal end. The blade is advanceable by movement of a blade trigger on the handle assembly. The at least one electrode on the first jaw and the at least one electrode on the second jaw have opposing polarity and define a fusion and/or dissection area enclosing the cutting or dividing path. In various embodiments, the jaw assembly is provided to fuse or seal when RF energy is applied and subsequently to cut tissue between the jaw members using a mechanical cutting blade.

In some embodiments, the electrosurgical tool can be used in a system which monitors various operational parameters and determines a radiofrequency endpoint based on phase angle and/or change of phase angle. The electrosurgical tool fuses vessels by delivering radio frequency (RF) energy to tissue grasped between the jaws of the device.

Further examples of the electrosurgical generator, unit, instruments and connections there between and operations and/or functionalities thereof are described in U.S. patent application Ser. No. 12/416,668, filed Apr. 1, 2009, entitled "Electrosurgical System"; Ser. No. 12/416,751, filed Apr. 1, 2009, entitled "Electrosurgical System"; Ser. No. 12/416,695, filed Apr. 1, 2009, entitled "Electrosurgical System"; Ser. No. 12/416,765, filed Apr. 1, 2009, entitled "Electrosurgical System"; and Ser. No. 12/416,128, filed Mar. 31, 2009, entitled "Electrosurgical System"; the entire disclosures of which are hereby incorporated by reference as if set in full herein. Certain aspects of these electrosurgical generators, tools and systems are discussed herein, and additional details and examples with respect to various embodiments are described in US Provisional Application Nos. 61/994,215, filed May 16, 2014, entitled "Electrosurgical Fusion Device"; 61/944,185, filed May 16, 2014, "Electrosurgical Generator with Synchronous Detector"; 61/944,192, filed May 16, 2014, entitled "Electrosurgical Generator"; 61/994,415, filed May 16, 2014, entitled "Electrosurgical System"; 62/005,009, filed May 30, 2014, entitled "Electrosurgical Laparoscopic Sealer and Dissector; and U.S. patent application Ser. No. 14/848,116, filed Sep. 8, 2015, entitled "Electrosurgical System"; the entire disclosures of which are hereby incorporated by reference as if set in full herein.

The above description is provided to enable any person skilled in the art to make and use the surgical tools and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. An electrosurgical instrument comprising:
    a lower handle having a proximal end, a distal end and a housing;
    an upper jaw coupled to the distal end of the lower handle, the upper jaw having a conductive pad and a decouplable portion of the housing of the lower handle being configured to be decoupled from the upper jaw;
    an upper handle having a proximal end, a distal end and a housing having a cavity; and
    a lower jaw coupled to the distal end of the upper handle, the lower jaw pivotably connected to the upper jaw and the upper and lower handles being arranged to be brought together from an open position, where the upper and lower jaws are open, to a closed position where the upper and lower jaws are closed;
    the upper handle comprising:
        a blade trigger;
        a blade slider;
        a blade lever arm connected to the blade trigger and the blade slider, in which movement of the blade trigger moves the blade lever arm which moves the blade slider, the blade slider being translatable longitudinally through a channel in the upper and lower jaws;
        a blade lock hook engageable with the blade trigger to prevent distal movement of the blade trigger, the blade lever arm, and the blade slider; the blade lock hook, the blade lever arm, the blade slider and a portion of the blade trigger being disposed within the cavity of the housing of the upper handle; and
        a switch arranged to contact the decouplable portion of the housing of the lower handle and to activate through contact with the decouplable portion of the housing of the lower handle to connect to a supply of RF energy;
    the decouplable portion of the housing of the lower handle comprising a blade unlock projection extending from an outer surface of the decoupled portion of the housing of the lower handle towards the upper handle, the blade unlock projection engageable with the blade lock hook disposed within the cavity of the housing of the upper handle to disengage the blade lock hook from the portion of the blade trigger disposed within the housing of the upper handle; and
    wherein the upper and lower handles are arranged to be brought closer together from the closed position to a fuse position, in that with the upper and lower handles being configured to be moved from the closed position to the fuse position, the decouplable portion of the housing of the lower handle is decoupled from the upper jaw and, in the fuse position, the blade unlock projection of the decouplable portion of the housing of the lower handle engages the blade lock hook to disengage the blade lock hook from the blade trigger permitting distal movement of the blade trigger, the blade lever arm and the blade slider, and an outer surface of the decouplable portion of the housing of the lower handle engages the switch of the upper handle.

2. The electrosurgical instrument of claim 1 further comprises a blade spring disposed within the cavity of the housing of the upper handle and connected to the blade trigger.

3. The electrosurgical instrument of claim 2 wherein the blade slider is aligned with a longitudinal axis of the electrosurgical instrument and the blade lever arm is angled relative to the longitudinal axis.

4. The electrosurgical instrument of claim 3 wherein the blade trigger is rotatable and the blade lever arm and the blade slider are translatable.

5. The electrosurgical instrument of claim 1 wherein the conductive pad of the upper jaw has a flat planar sealing surface facing the lower jaw.

6. The electrosurgical instrument of claim 5 wherein the lower jaw comprises a conductive pad having a flat planar sealing surface facing the upper jaw and operationally arranged to transmit RF energy between the conductive pad of the upper jaw and the conductive pad of the lower jaw.

7. The electrosurgical instrument of claim 6 wherein the lower jaw further comprises a lower assembly spacer and a conductive post positioned within the lower assembly spacer.

8. The electrosurgical instrument of claim 7 wherein the conductive post is positioned adjacent to the lower conductive pad.

9. The electrosurgical instrument of claim 8 wherein the lower jaw further comprises an overmold covering the lower jaw support and the lower assembly spacer.

10. The electrosurgical instrument of claim 9 wherein the upper jaw further comprises an upper jaw support and an assembly spacer positioned between positioned between the upper jaw support and the conductive pad of the upper jaw.

11. The electrosurgical instrument of claim 10 wherein the upper jaw further comprises an overmold covering the upper jaw support and the assembly spacer of the upper jaw.

12. The electrosurgical instrument of claim 11 wherein the conductive pad of the upper jaw has a total surface area larger than a total surface area of the conductive pad of the lower jaw.

13. The electrosurgical instrument of claim 11 further comprising a central pivot connecting the upper handle to the lower handle and connecting the upper jaw to the lower jaw, the central pivot having an opening through which the blade slider is configured to be extendable and retractable there through.

14. The electrosurgical instrument of claim 13 wherein the central pivot has a circular end inserted and connected to a circular opening in the upper jaw support and a non-circular end inserted and connected to a non-circular opening in the lower jaw support.

15. The electrosurgical instrument of claim 14 wherein the circular end is configured to allow the upper jaw support to pivot about the central pivot and the non-circular end is configured to resist pivoting of the lower jaw support about the central pivot such that as the upper jaw connected to the upper jaw support is pivotable from a proximate position to a spaced position and vice versa, the lower jaw remains stationary due to its connection to the lower jaw support and the non-circular end of the central pivot.

16. The electrosurgical instrument of claim 15 wherein the lower jaw support comprises a guide channel dimensioned to receive and support the blade slider, the guide channel aligning and supporting the longitudinal translation of the blade slider.

17. The electrosurgical instrument of claim 16 further comprising a pin connecting the blade slider to the blade lever arm and wherein the lower jaw support further comprises a proximal pin channel at a proximal end of the lower jaw support, the proximal pin channel dimensioned to receive and support the pin connecting the blade slider to the blade lever arm, the proximal pin channel aligning and supporting the longitudinal translation of the blade slider.

18. The electrosurgical instrument of claim 17 further comprising wires extending from the switch through the cavity of the housing of the upper handle, the upper and lower jaw supports to the upper and lower jaws and the conductive pad of the upper jaw and the conductive pad of the lower jaw, bypassing the housing of the lower handle.

19. The electrosurgical instrument of claim 18 further comprising a support arm having a distal connected to the upper jaw support and a proximal portion enclosed in the housing of the lower handle.

20. The electrosurgical instrument of claim 19 wherein the support arm includes a slot and the lower handle comprises a pin disposed within the slot of the support arm, the pin and the slot being operatively movable relative to each other as the upper and lower handles are moved from the closed position to the fuse position.

* * * * *